US010709904B2

(12) United States Patent
Limousin et al.

(10) Patent No.: US 10,709,904 B2
(45) Date of Patent: Jul. 14, 2020

(54) APPARATUS FOR PERFORMING NANOPARTICLE-ASSISTED EXTERNAL BEAM RADIOTHERAPY AND METHOD CARRIED OUT USING SAID APPARATUS

(71) Applicant: COMMISSARIAT A L'ENERGIE ATOMIQUE ET AUX ENERGIES ALTERNATIVES, Paris (FR)

(72) Inventors: Olivier Limousin, Palaiseau (FR); Daniel Maier, Paris (FR); Diana Renaud, Gif-sur-Yvette (FR); Romain Grall, Paris (FR); Sylvie Chevillard, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/203,534

(22) Filed: Nov. 28, 2018

(65) Prior Publication Data

US 2019/0175948 A1 Jun. 13, 2019

(30) Foreign Application Priority Data

Dec. 7, 2017 (EP) .................................. 17290157

(51) Int. Cl.
*A61N 5/10* (2006.01)
*A61B 6/00* (2006.01)

(52) U.S. Cl.
CPC .......... *A61N 5/1071* (2013.01); *A61B 6/4042* (2013.01); *A61B 6/482* (2013.01);
(Continued)

(58) Field of Classification Search
CPC ..... A61B 6/4042; A61B 6/4241; A61B 6/482; A61B 6/483; A61B 6/485; A61N 5/1049;
(Continued)

(56) References Cited

U.S. PATENT DOCUMENTS

2012/0307962 A1 12/2012 Cho et al.
2013/0010927 A1 1/2013 Seppi et al.
(Continued)

FOREIGN PATENT DOCUMENTS

EP 2 078 537 A1 7/2009

OTHER PUBLICATIONS

Cheng et al., "Chemical enhancement by nanomaterials under x-ray irradiation", Journal of the American Chemical Society, 134(4), pp. 1950-1953, 2012.
(Continued)

*Primary Examiner* — Mark R Gaworecki
(74) *Attorney, Agent, or Firm* — Baker & Hostetler LLP

(57) ABSTRACT

An apparatus for performing nanoparticle-assisted external beam radiotherapy includes an X-ray spectrometer having an optical axis, an X-ray filter, and a mobile holding structure for holding the X-ray filter and X-ray spectrometer in a first and second relative position, and for switching from the first to second relative position while simultaneously positioning a patient body part in a target region including a target point. An X-ray beam emitted from the X-ray source crosses the X-ray filter before reaching the target point. The propagation of the X-ray beam forms an angle different from 0° and 180° with the optical axis of the X-ray spectrometer. The second relative position is obtained by inverting the relative positions of the X-ray filter and X-ray spectrometer relative to the patient body part. A method of determining an X-ray dose delivered at a region of a patient body using the apparatus is provided.

14 Claims, 15 Drawing Sheets

(52) U.S. Cl.
CPC ............ *A61B 6/485* (2013.01); *A61N 5/1049* (2013.01); *A61B 6/4241* (2013.01); *A61B 6/483* (2013.01); *A61N 2005/1054* (2013.01); *A61N 2005/1091* (2013.01); *A61N 2005/1095* (2013.01); *A61N 2005/1098* (2013.01); *G01N 2223/076* (2013.01)

(58) Field of Classification Search
CPC .......... A61N 5/1071; A61N 2005/1054; A61N 2005/1091; A61N 2005/1095; A61N 2005/1098; G01N 2223/076
See application file for complete search history.

(56) References Cited

U.S. PATENT DOCUMENTS

2016/0252471 A1  9/2016  Guo et al.
2017/0245819 A1  8/2017  Rothschild et al.

OTHER PUBLICATIONS

Hernandez, et al., "Tungsten anode spectral model using interpolating cubic splines: Unfiltered x-ray spectra from 20 kV to 640 kV", Medical Physics, vol. 41, No. 4, pp. 042101-1-15, Apr. 2014.

APPARATUS FOR PERFORMING NANOPARTICLE-ASSISTED EXTERNAL BEAM RADIOTHERAPY AND METHOD CARRIED OUT USING SAID APPARATUS

CROSS-REFERENCE TO RELATED APPLICATIONS

This application claims priority to foreign European patent application No. EP 17290157.1, filed on Dec. 7, 2017, the disclosure of which is incorporated by reference in its entirety.

FIELD OF THE INVENTION

The invention relates to an apparatus for performing nanoparticle-assisted external beam radiotherapy and to a dosimetry method carried out using said apparatus.

BACKGROUND

Radiotherapy, or radiation therapy, is a cancer treatment wherein ionizing radiation is used to control or kill malignant cells. Ionizing radiation works by damaging the DNA, as well as other biomolecules, of cancerous cells both directly (e.g. radiation can directly brake DNA strands) and indirectly, by generating free radicals through water radiolysis; the free radicals subsequently attacking the DNA and other biomolecules.

Radiotherapy may be curative in localized cancer or palliative for reducing pain in case of cancer spreading and metastases. It is also used before surgery to reduce the volume of the tumor and could be part of adjuvant therapy to prevent tumor recurrence after surgery. Radiation therapy is often combined with chemotherapy, with which it is synergistic.

External beam radiotherapy is the most common form of radiotherapy. It uses ionizing radiation—most often X-rays, but sometimes electron or proton beams—generated by an external source (e.g. an X-ray tube or a linear accelerator) pointed at a target region of the patient's body. In contrast to sealed source radiotherapy and unsealed source radiotherapy, in which the radiation source is inside the body, external beam radiotherapy directs the radiation at the tumor from outside the body. The energy of the ionizing radiation depends on the depth of target tumor. For X-rays it may vary from several tens of keV (kiloelectronvolts) to several MeV (megaelectronvolts).

It is known that metal (usually gold) nanoparticles localized in the target tumor may enhance the therapeutic effect of ionizing radiation. On the one hand, this is due to the fact that the metal nanoparticles enhance X-ray absorption in the tumor; on the other hand, when irradiated, they emit electrons which increase the radiolysis rate.

Nanoparticles tend to accumulate in cancer cells due to the Enhanced Permeability and Retention Effect characterizing said cells. They can also be injected into the tumor or functionalized at their surface to increase the specificity of their localization. Their size is not critical for radiotherapy; however a diameter of less than 6 nm is preferred to ease their elimination from the body.

A drawback of external beam radiotherapy is that the dose delivered to the target region of the body cannot be measured, but only be estimated a priori using physical modeling. The estimation is unavoidably affected by a significant uncertainty, which limits the scope for optimizing the therapeutic protocol.

SUMMARY OF THE INVENTION

The invention aims at overcoming this drawback in the case of nanoparticle-assisted X-ray external beam radiotherapy. More specifically, it aims at making possible an (at least indirect) measurement of the delivered X-ray dose and, preferably, of the mass of the nanoparticles within the treated region of the patient's body.

The invention relies on the fact that irradiated nanoparticles emit low-energy (<100 keV) X-ray fluorescence (XRF) radiation, which can be detected outside the patient's body. Measuring the intensity ratio of two different fluorescence lines allows quantifying the X-ray absorption of the patient's body from the tumor region to the detection. By performing two measurements with inverted relative positions of the source and of the detector relative to the treated region of the patient's body, and assuming that the spectral flux density (in units [photons/time/area/bandwidth]) of the source is known (e.g. from direct measurement, or by precise modeling of the source), it is possible to determine the delivered dose and the quantity of the fluorescent material (metal nanoparticles) in the target region.

According to the invention, an X-ray filter disposed between the source and the target region is used to increase the signal-to-noise ratio of the fluorescence measurements.

An object of the present invention, allowing achieving this aim, is an apparatus for performing nanoparticle-assisted external beam radiotherapy comprising:
- an X-ray spectrometer having an optical axis;
- an X-ray filter;
- a mobile holding structure suitable for holding the X-ray filter and the X-ray spectrometer in a first and a second relative position, and for switching from said first to said second relative position while simultaneously allowing the positioning of a patient body part in a target region including a target point;

wherein:
- the first and second relative positions of the X-ray filter and the X-ray spectrometer are such that an X-ray beam emitted from the X-ray source crosses the X-ray filter before reaching the target point, a propagation direction of the X-ray beam forming an angle $\theta$ different from 0° and 180° with the optical axis of the X-ray spectrometer; and
- the second relative position is obtained by inverting the relative positions of the X-ray filter and of the X-ray spectrometer with respect to the patient body part.

Another object of the invention is a method of determining an X-ray dose delivered at a region of a patient body using such an apparatus, the region of the patient body being positioned at the target point of the apparatus, the method comprising the steps of:
- setting the apparatus in a first configuration, corresponding to said first relative position of the X-ray filter and the X-ray spectrometer;
- activating the X-ray source, and using the X-ray spectrometer to acquire first data representing a first X-ray spectrum;
- setting the apparatus in a second configuration, corresponding to said second relative position of the X-ray filter and the X-ray spectrometer;
- activating the X-ray source, and using the X-ray spectrometer to acquire second data representing a second X-ray spectrum; and
- processing said first and second data to determine an X-ray dose delivered at a target region surrounding the target point by the apparatus.

Particular embodiments of the inventive apparatus and method constitute the subject-matter of the dependent claims.

BRIEF DESCRIPTION OF THE DRAWINGS

Additional features and advantages of the present invention will become apparent from the subsequent description, taken in conjunction with the accompanying drawings, which show.

DETAILED DESCRIPTION

Figure 1A:
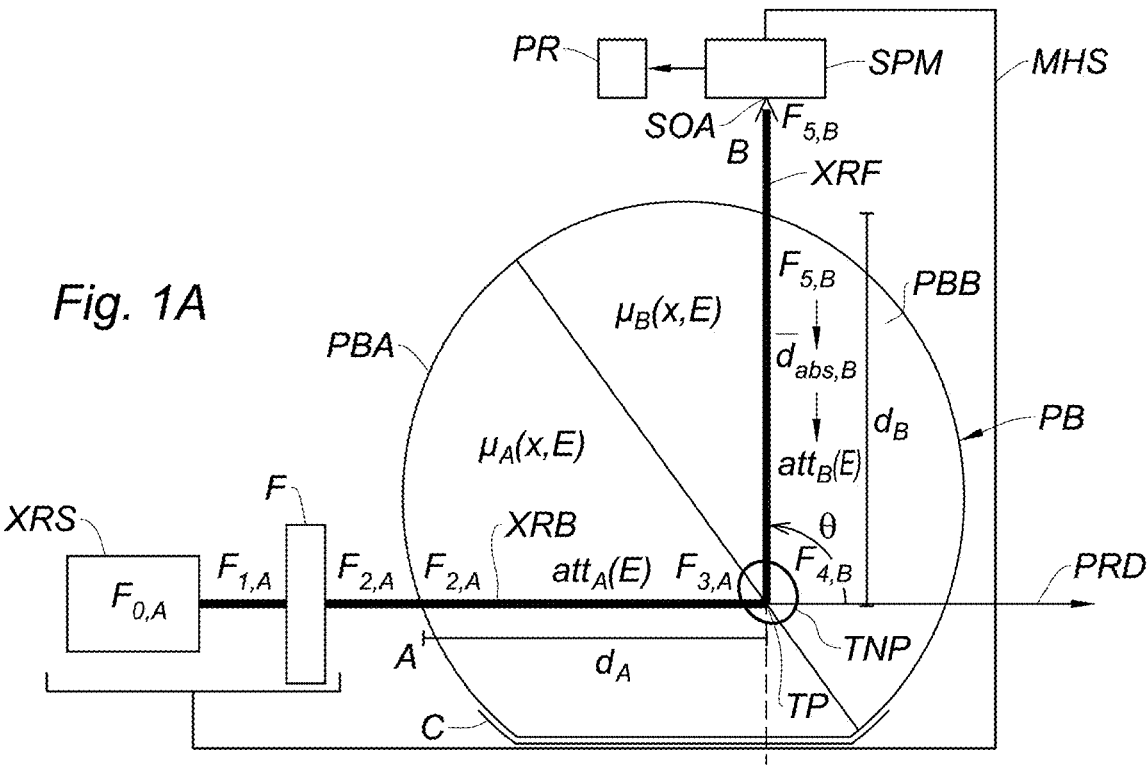
FIGS. 1A and 1B, an apparatus according to an embodiment of the invention in its first (1A) and second (1B) configuration.
Figure 1B:
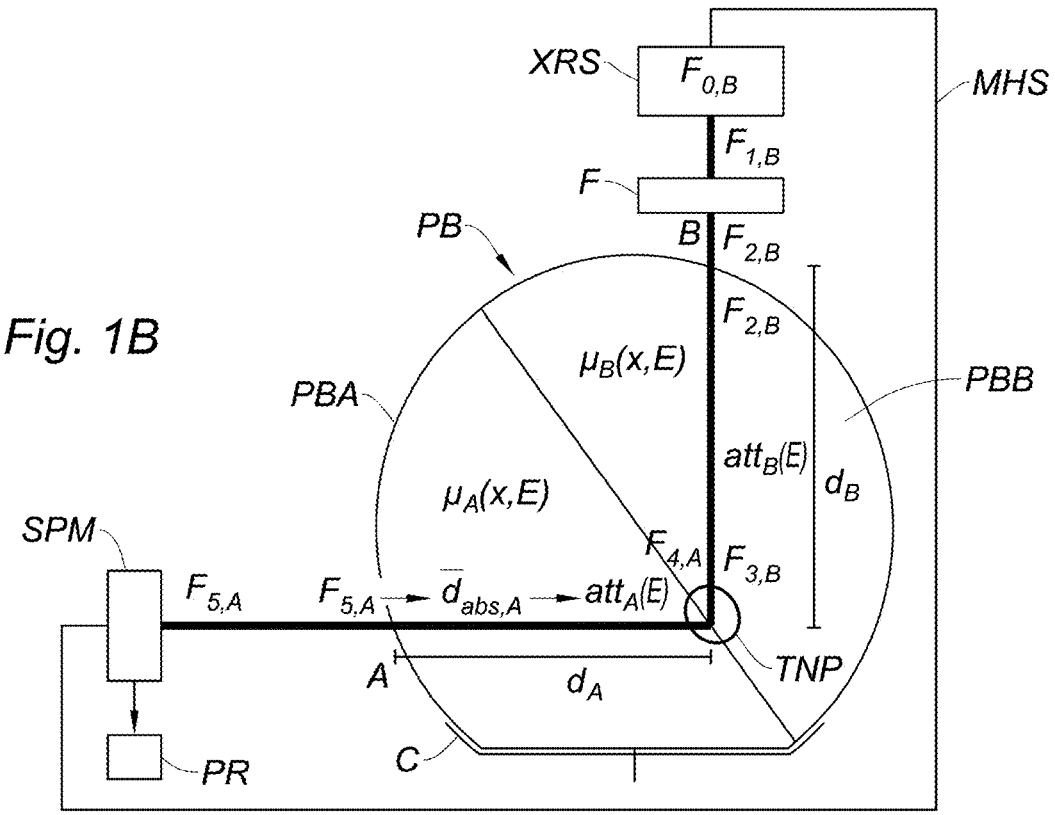

As illustrated on FIGS. 1A and 1B, an external radiotherapy apparatus according to the invention comprises:

an X-ray source XRS, such as a conventional radiotherapy X-ray tube (alternatively, an external X-ray source may be fitted to the apparatus), adapted for generating an X-ray beam XRB propagating along a propagation direction PRD. Typically, the X-ray source XRS operates in the orthovoltage (200-500 keV) or megavoltage (1-6 MeV) range.

An X-ray filter F, disposed on the propagation path of the X-ray beam—the design of this filter will be discussed extensively.

An X-ray spectrometer SPM, sensible in all or part of the 7-130 keV spectral range. Indeed, for all nanoparticle materials of interest, $K_{\alpha}$ and $K_{\beta}$ fluorescence lines are comprised in the 10-100 keV, and it is preferable that the spectrometer is sensitive in a region of at least ±30% of this range.

The spectrometer SPM has an optical axis SOA which forms an angle θ with the propagation direction PRD. The angle θ is significantly different from zero. Preferably it is greater than or equal to 90° when measured considering that the optical axis SOA is directed toward the spectrometer. The criteria for determining the optimal value of θ will be discussed later.

The propagation direction PRD and the optical axis SOA cross at a target point TP. When the apparatus is used, a body part PB of a cancer patient, previously treated with metal nanoparticles, is positioned on the path of the X-ray beam in such a way that a nanoparticle-loaded tumor TNP is situated at the target point. This way, X-rays impinging on the tumor excite X-ray fluorescence of the metal nanoparticles localized in the tumor; the spectrometer detects and analyzes the X-ray fluorescence radiation XRF emitted along its optical axis SOA.

The X-ray source, the filter, the spectrometer and possibly a couch, armchair or the like (reference C on FIGS. 1A and 1B) for receiving the patient are hold by a moving holding structure MHS, such as a conventional gantry. The holding structure must be suitable to invert the relative positions of the X-ray source/filter and of the X-ray spectrometer with respect to the patient body part. FIG. 1A shows a first configuration of the apparatus, wherein the X-ray source/filter ensemble occupies a position "A" with respect to the patient's body, and the spectrometer a position "B". FIG. 1B shows a second configuration of the apparatus, inverted with respect to the first one, wherein the X-ray source/filter ensemble occupies position "B" with respect to the patient's body, and the spectrometer position "A". The switching from the first to the second configuration (or vice-versa) can be performed by moving (typically, rotating) the X-ray source/filter ensemble and the X-ray spectrometer while keeping the patient still. Alternatively, it is possible to rotate the spectrometer and the couch/armchair on which the patient rests while keeping the X-ray source and filter still, or even to rotate the X-ray source and filter and the couch/armchair while keeping the spectrometer still.

When the apparatus is in its first configuration, the X-ray beam XRB crosses, on its way to the tumor, a first portion PBA of the patient's body part, characterized by a position (x) and energy (E) dependent absorption coefficient $\mu_A(x,E)$. The propagation length inside the first portion PBA is designated by $d_A$ and the overall energy-dependent attenuation by $att_A(E)$. The X-ray fluorescence radiation XRF originating from the nanoparticles inside the tumor crosses, on its way to the spectrometer, a second portion PBB of the patient's body part, characterized by a position (x) and energy (E) dependent absorption coefficient $\mu_B(x,E)$. The propagation length inside the second portion PBB is designated by $d_B$ and the overall energy-dependent attenuation by $att_B(E)$. In the second configuration of the apparatus, the roles of the first and second portions of the patient's body are exchanged.

A processor PR is configured to receive spectral data from the X-ray spectrometer in the two configurations of the apparatus, and use these data to compute the X-ray dose delivered to the tumor, and preferably also the mass of the metal nanoparticles. These computations will be described in detail later.

In the following, position index $P \in \{A,B\}$ will be used to designate either the first configuration (source at point A) or the second configuration (source at point B).

On FIGS. 1A and 1B:

$F_0$ designates the "internal" X-ray flux of the source, and $F_0(E)$ the corresponding spectral flux density. In principle, $F_0$ may not be the same in the first and in the second configuration, therefore $F_{0,P}$ (i.e; $F_{0,A}$ and $F_{0,B}$) will be used in the following. $F_0(E)$ is a function of the acceleration voltage U and of the operation current I of the X-ray source (tube).

$F_{1,P}$ (i.e. $F_{1,A}$ and $F_{1,B}$) designates the "primary" X-ray flux of the source, taking into account internal absorption (e.g. from the anode and the housing) and $F_{1,P}(E)$ the corresponding spectral flux density.

$F_{2,P}$ (i.e. $F_{2,A}$ and $F_{2,B}$) designates the "filtered" X-ray flux, taking into account the absorption from filter F. $F_{2,P}(E)$ is the corresponding spectral flux density.

$F_{3,P}$ (i.e. $F_{3,A}$ and $F_{3,B}$) designates the X-ray flux reaching the tumor, taking into account the absorption from bodily tissues of the first portion PBA (in the first configuration of the apparatus) or of the second portion PBB (in the second configuration of the apparatus) of the patient's body part. $F_{3,P}(E)$ is the corresponding spectral flux density.

$F_{4,P}$ (i.e. $F_{4,A}$ and $F_{4,B}$) designates the X-ray fluorescence flux emitted by the metal nanoparticle inside the tumor. $F_{4,P}(E)$ is the corresponding spectral flux density.

$F_{5,P}$ (i.e. $F_{5,A}$ and $F_{5,B}$) designates the X-ray fluorescence flux reaching the spectrometer, taking into account the absorption from bodily tissues of the second portion PBB (in the first configuration of the apparatus) or of the first portion PBA (in the second configuration of the apparatus) of the patient's body part. $F_{5,P}(E)$ is the corresponding spectral flux density.

$F_{5,A}$ and $F_{5,B}$ are the measured quantities, from which $F_{3,A}$ and $F_{3,B}$—and therefore the radiometric dose—as well as the nanoparticles mass $m_{np}$ can be computed, as it will be explained in detail.

In the following, the geometrical flux attenuation of the X-ray beam is not taken into account but can be easily included in the consideration knowing the beam properties (spot size, divergence) and the geometry of the setup.

The interaction probability between X-rays and matter can be described with Beer's law. According to this, an initial flux $F_0$ is attenuated to $$F(x,E) = F_0(E) \cdot e^{-\mu(E)x} \quad (1)$$

after passing a length x through matter with an attenuation coefficient $\mu$. The attenuation length $$\lambda = 1/\mu \quad (2)$$

describes an attenuation to $e^{-1} \approx 36.8\%$ (or "by $1-e^{-1}$") and can be interpreted as a mean interaction length.

Figure 6A:
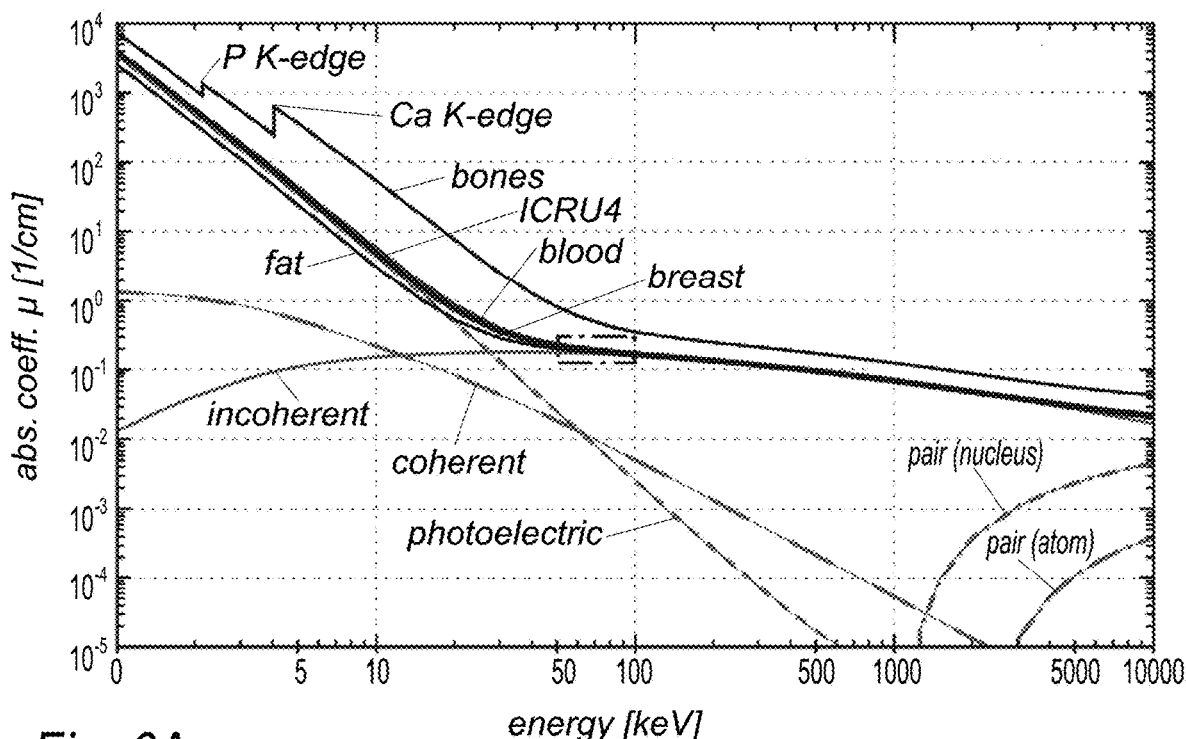
FIGS. 6A and 6B, plots of the total absorption coefficient of ICRU 4-component soft human tissue and its decomposition into different contributions; total absorption coefficients for other human tissues are also represented for comparison.
Figure 6B:
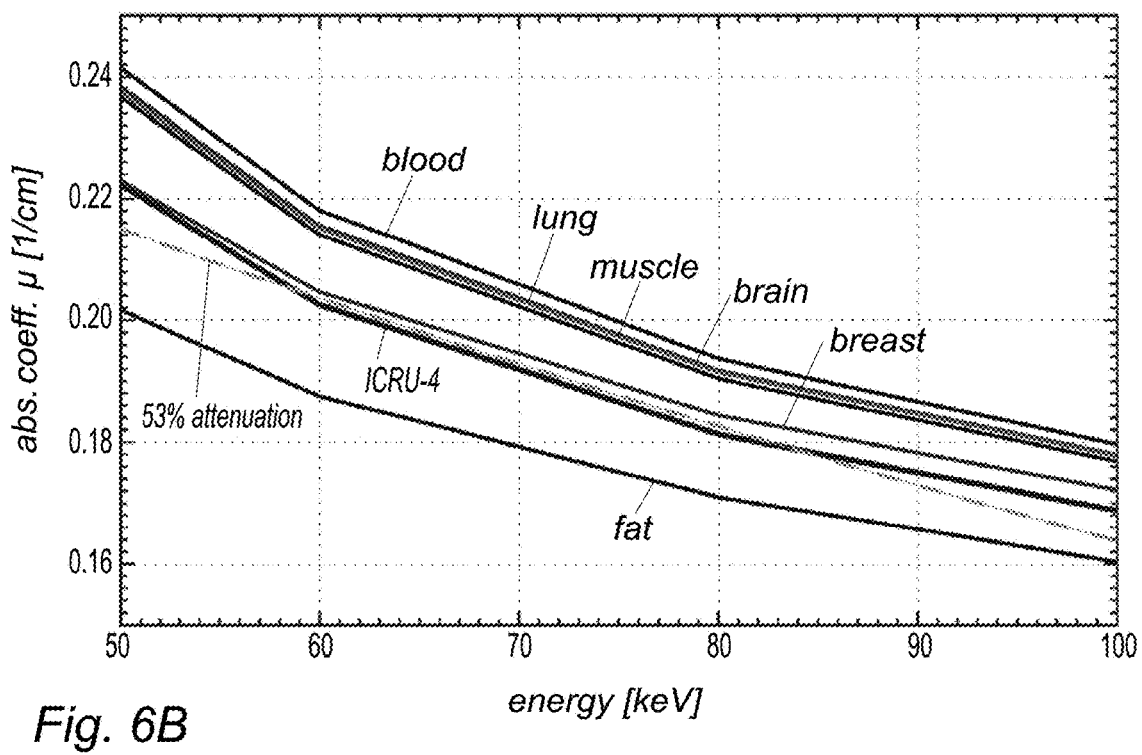

FIGS. 6A and 6B plot the attenuation coefficients for the interactions between X-rays and several soft human tissues as a function of photon energy according to the well-known ICRU-4, or "ICRU four component" model) and its decomposition into different contributions: coherent scattering, incoherent scattering, photoelectric absorption, pair creation from nuclei and atoms. Only bones show clear absorption edges of P and Ca. Absorption edges in soft tissue (fat, blood, and breast) are almost invisible in this scale. The total ICRU-4 absorption coefficient is also plotted (thickest line).

FIG. 6B shows a zoom into a range of interest with additional tissues (lung, muscle, brain). Except for bones, the differences in absorption are within ±10% compared to ICRU-4. The mean variation of the attenuation coefficient of ICRU-4 component tissue can be well approximated by a constant attenuation of 5.3% per 10 keV within the energy interval 60<E [keV]<80 (dashed line on FIG. 6B).

The range of the zoom of FIG. 6B is also indicated by a rectangle on FIG. 6A

For energies E≥50 keV incoherent scattering becomes the dominant effect with a mean interaction length $\lambda \geq 4$ cm.

These number demonstrate that soft human tissue has an absorption coefficient which is relatively constant within the energy range of XRF (50 keV<E<100 keV).

Figure 7:
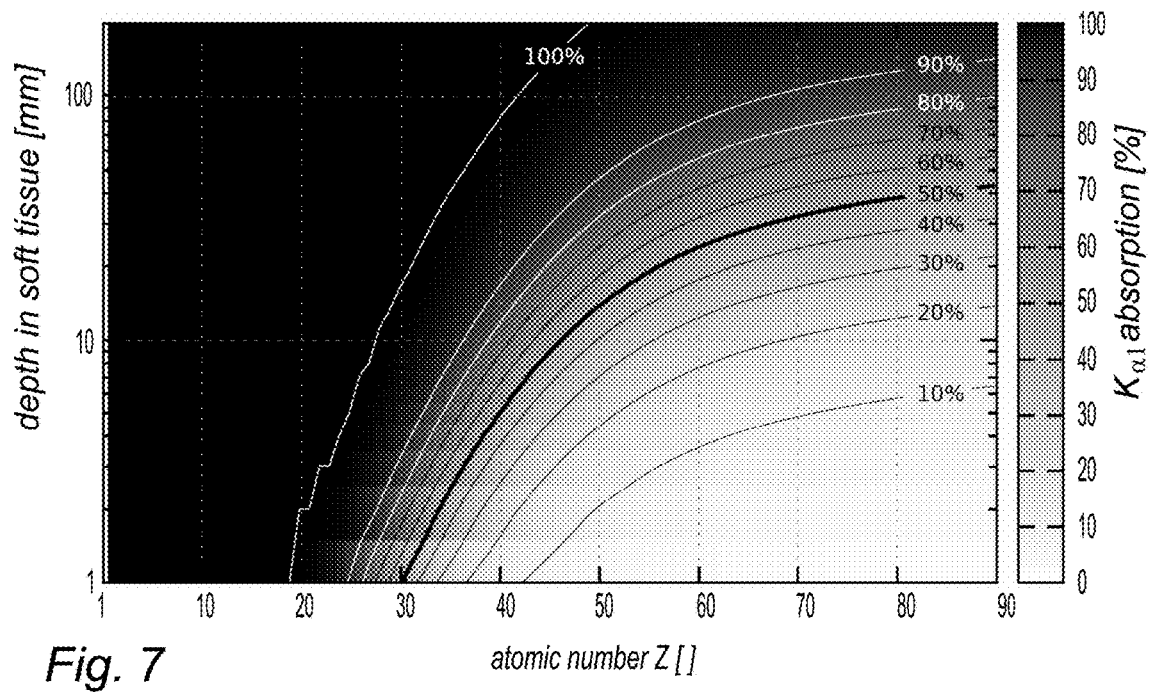
FIG. 7, a density map of $K_{\alpha 1}$ absorption in ICRU 4-component soft human tissue as a function of atomic number Z of the metal nanoparticle and tumor depth.

FIG. 7 is a density plot of the $K_{\alpha 1}$ absorption as a function of penetration depth in ICRU-4 soft tissue and atomic number. It can be seen that elements with Z<20 cannot be used, as the corresponding XRF radiation is completely absorbed even by a negligible depth of soft tissue. Use of elements with Z<30 is generally impractical, and elements with Z≥50 will be preferred.

X-ray attenuation is present for the incoming beam and for the outgoing XRF radiation even though the energies can be quite different (i.e. the X-ray beam can have energies of several hundreds of keV up to several MeV).

The filtered flux $F_{2,P}$ is considered to be, a priori, well known. This might be the case because of a well calibrated tube and filter setup or by direct flux measurement or any combination of both. The subsequent fluxes can be calculated in the following way:

$$F_{3,P}(E) = F_{2,P}(E) \cdot \exp\left(-\int_0^{d_P} \mu_P(x,E)dx\right) := F_{2,P}(E) \cdot e^{-att_P(E)} \quad (3)$$

$$F_{4,P}(E) = F_{3,P}(E) \cdot G(E, m_{np}, Z_{np}) \quad (4)$$

$$F_{5,P}(E) = F_{4,P}(E) \cdot \exp\left(-\int_0^{d_P} \mu_P(x,E)dx\right) := F_{4,P}(E) \cdot e^{-att_P(E)} \quad (5)$$

where ":=" means "is defined by".

The attenuation factors $\mu_P(x,E)$ along the beam path and along the XRF escape path are unknown. Only their integral contributions, i.e. the attenuations $att_P$, are of interest:

$$att_P(E) = \int_0^{d_P} \mu_P(x, E)dx \text{ for } P \in \{A, B\} \quad (6)$$

Even though the $att_P$ are unknown, their energy dependence, i.e. their spectral shape, can be considered to be well described by existing models for soft tissue (e.g the already discussed ICRU-4 component model).

The introduction of a mean attenuation length (represented on FIGS. 1A and 1B) such that $$att_A(E) \approx \mu_{model}(E) \cdot \overline{d}_{abs,A} \text{ and } att_B(E) \approx \mu_{model}(E) \cdot \overline{d}_{abs,B} \quad (7)$$

allows describing the energy dependence of the attenuation by a model while the intensity of the attenuation is set with the constant factor $\overline{d}_{abs,P}$ which will be determined during the measurement, see below. The constant $\overline{d}_{abs,P}$ not only averages the locally different attenuation factors, but is also a measurement of the distances $d_P$.

The fluorescence generator function $G(E, m_{np}, Z_{np})$ depends on the cross section for photoelectric interaction $\sigma_{PE}(E)$, which itself depends on the photon energy E, the total mass of the fluorescence particles $m_{np}$ within the primary beam, and the fluorescence yield $y(Z)$ of the fluorescence element.

$$G(E, m_{np}, Z_{np}) = \frac{m_{np}}{m_{atom}} \cdot \frac{\sigma_{PE}(E) \cdot y(Z_{np})}{4\pi r^2} \quad (8)$$

where r is the distance from the detector and the target point (estimated e.g. using independently-acquired tomographic information) and $m_{atom}$ is the atomic mass number of the metal element constituting the nanoparticles. If the nanoparticles are made of an alloy, individual fluorescence generator functions will be computed for each element of the alloy.

The mean attenuation constant $\overline{d}_{abs,P}$ is used to define the body attenuation according to Eq. (7). This is done by computing the relative flux attenuation at two different energies within the measured spectral flux density $F_5(E)$. For this purpose, the non-attenuated flux ratio at these energies must be clearly defined, while the non-attenuated flux itself can be unknown. The $K_\alpha$ and $K_\beta$ XRF line emissions fulfill this requirement as their ratio is a material dependent constant. The energy difference between the two lines results in a slightly less attenuated $K_\beta$ flux compared to the $K_\alpha$ flux. The $K_{\beta 1}$-to-$K_{\alpha 1}$ ratio $\eta$ is used to quantify the ratio between the two fluxes, while $\delta_\eta$ represents the ratio between $\eta(d)$—the $K_{\beta 1}$-to-$K_{\alpha 1}$ ratio after some absorption in ICRU4 tissue—and the unabsorbed $\eta_0$.

$$\mu_\alpha := \mu_{ICRU4}(E_{K_{\alpha 1}}) \quad (9)$$
$$\mu_\beta := \mu_{ICRU4}(E_{K_{\beta 1}})$$

$$F_{\alpha 0} := F_4(E_{K_{\alpha 1}}, 0) \quad (10)$$
$$F_{\beta 0} := F_4(E_{K_{\beta 1}}, 0)$$

$$\eta_0 := \eta(0) := \frac{F_{\beta 0}}{F_{\alpha 0}} = const. \quad (11)$$

$$\eta(d) = \frac{F_5(E_{K_{\beta 1}}, d)}{F_5(E_{K_{\alpha 1}}, d)} \quad (12)$$

$$= \frac{F_{\beta 0} \cdot e^{-\mu_\beta \cdot d}}{F_{\alpha 0} \cdot e^{-\mu_\alpha \cdot d}}$$

$$= \eta_0 \cdot e^{-(\mu_\beta - \mu_\alpha)d}$$

$$\delta_\eta(d) = \frac{\eta(d)}{\eta_0} = e^{-(\mu_\beta - \mu_\alpha)d} \quad (13)$$

Figures 2A, 2B, 2C:
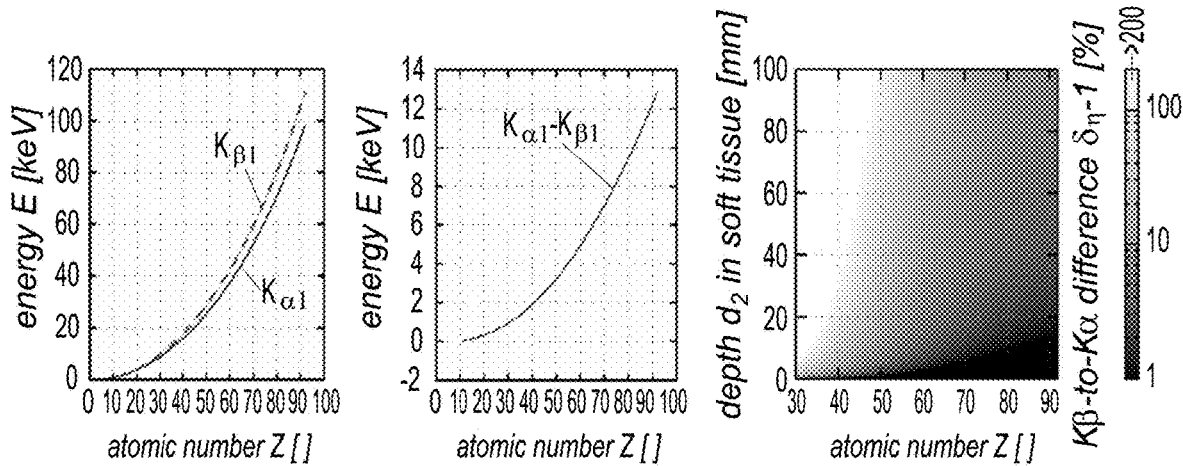
FIG. 2A, a plot of the $K_{\alpha 1}$ and $K_{\beta 1}$ energies as a function of atomic number Z.
FIG. 2B, a plot of the energy difference between said energies, also as a function of atomic number Z.
FIG. 2C; a density map of the flux ratio difference as a function of atomic number Z of the metal nanoparticle and of the target point depth inside the patient's body.

It is worth mentioning that the relative change $\delta_\eta$ does not depend on the initial flux ratio $\eta_0$. FIG. 2A shows the energy of the $K_{\alpha 1}$ and $K_{\beta 1}$ fluorescence lines as a function of atomic number; FIG. 2B, the difference of these energies and FIG. 2C the resulting flux ratio difference $\delta_\eta$ as a function of the absorption length in soft tissue (ICRU4) and the atomic number Z.

Even though the difference between $K_{\alpha 1}$ and $K_{\beta 1}$ are getting smaller at lower Z, $\delta_\eta$ increases for lower Z because of the stronger absorption at lower energies.

Besides the relative change $\delta_\eta$, noise is another important factor that limits the detection capability of $\overline{d}_{abs,P}$. The counting uncertainty can be estimated by combining the propagation of error with the Poisson distribution. For $a = F_5(K_\alpha)$ and $b = F_5(K_\beta)$ it follows $$\eta = \frac{b}{a} \to \Delta\eta = \sqrt{\left(\frac{-b}{a^2}\Delta a\right)^2 + \left(\frac{\Delta b}{a}\right)^2} = \sqrt{\frac{b^2}{a^3} + \frac{b}{a^2}} \quad (14)$$

Figures 3A, 3B, 3C, 3D:
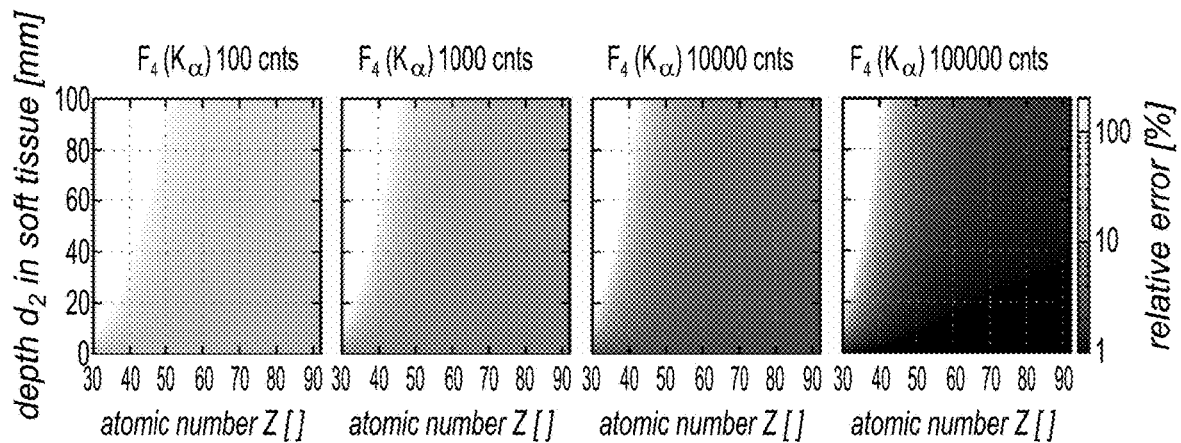
FIGS. 3A-3D, density maps of a relative uncertainty affecting the flux ratio between $K_{\alpha 1}$ and $K_{\beta 1}$ ray intensities as a function of atomic number Z of the metal nanoparticle and of the target point depth inside the patient's body.
Figures 10A, 10B, 10C:
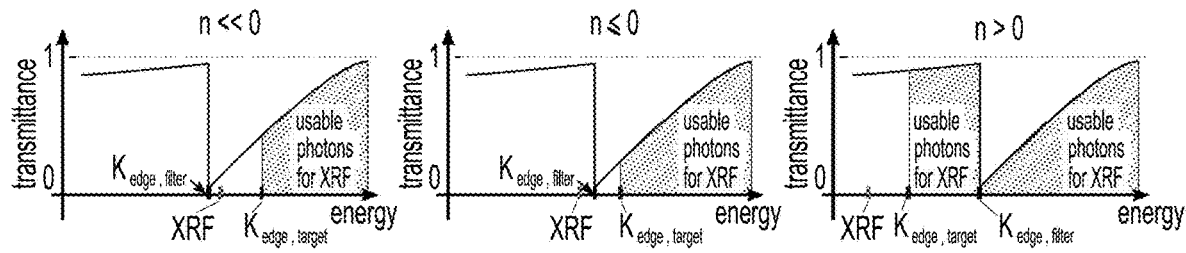
FIGS. 10A, 10B and 10C, the positions of X-ray fluorescence ray and plots of X-ray filter transmittances for different target/filter combinations in the case of no scattering (θ=0)

The relative uncertainty $\Delta\eta rel$ is finally given by:

$$\Delta\eta_{rel} = \frac{\Delta\eta}{b/a} \quad (15)$$

which is shown on FIGS. 3A, 3B, 3C and 3D for different statistics of the fluorescence flux $F_4$ (100 counts for FIG. 3A, 1000 counts for FIG. 3B, 10,000 counts for FIG. 3C and 100,000 counts for FIG. 3D).

The flux ratio $\eta_A$ and $\eta_B$ can be directly measured for the two beam-detector positions, without the need of knowing the length $d_A$ or $d_B$ of the absorbing tissue:

$$\eta_A = \frac{F_{5,A}(E_{K_{\beta 1}})}{F_{5,A}(E_{K_{\alpha 1}})} \text{ and } \eta_B = \frac{F_{5,B}(E_{K_{\beta 1}})}{F_{5,B}(E_{K_{\alpha 1}})} \quad (16)$$

In fact, equivalent length $\overline{d}_{abs,P}$ represents the mean attenuation for the tissue absorption $a_A$ and $a_B$. From Eq. (13) it follows $$\overline{d}_{abs,A} = \frac{\ln\left(\frac{\eta_A}{\eta_0}\right)}{\mu_\alpha - \mu_\beta} \text{ and } \overline{d}_{abs,B} = \frac{\ln\left(\frac{\eta_B}{\eta_0}\right)}{\mu_\alpha - \mu_\beta} \quad (17)$$

which can be used (see equations 3 and 7) to find $F_{3,A}$ and $F_{3,B}$.

The dosimetric quantity "kerma" (Kinetic Energy Released per MAss) K is defined as the quotient of $dE_{tr}$ by dm, where $dE_{tr}$ is the mean sum of the initial kinetic energies of all the charged particles liberated in a mass dm of a material by the uncharged particles incident on dm, thus $$K := \frac{dE_{tr}}{dm} \quad (18)$$

It can be calculated [Hubbell and Seltzer, 1995, 1999] as an integral value of the flux at the tumor position using the mass energy-transfer coefficient, $\mu_{tr}/\rho$:

$$K_P = \int_0^{E_{max}} F_{3,P}(E) \cdot E \cdot \Delta t_P \cdot \frac{\mu_{tr}(E)}{\rho} dE \text{ for } P \in \{A, B\} \quad (19)$$

$$K = K_A + K_B. \quad (20)$$

Here $F_{3,P}(E) \cdot E \cdot \Delta t_P$ defines the photon energy fluence calculated as the product of the flux $F_{3,P}$, the photon energy E, and the beam-on time $\Delta t_P$ in configuration P.

The kerma does not take into account that some fraction of the kinetic energy can escape—for example by Bremsstrahlung—from mass element dm. The mass energy absorption coefficient involves this effect and is defined as:

$$\mu_{en}/\rho = (1-g) \cdot \mu_{tr}/\rho. \quad (21)$$

Figure 4:
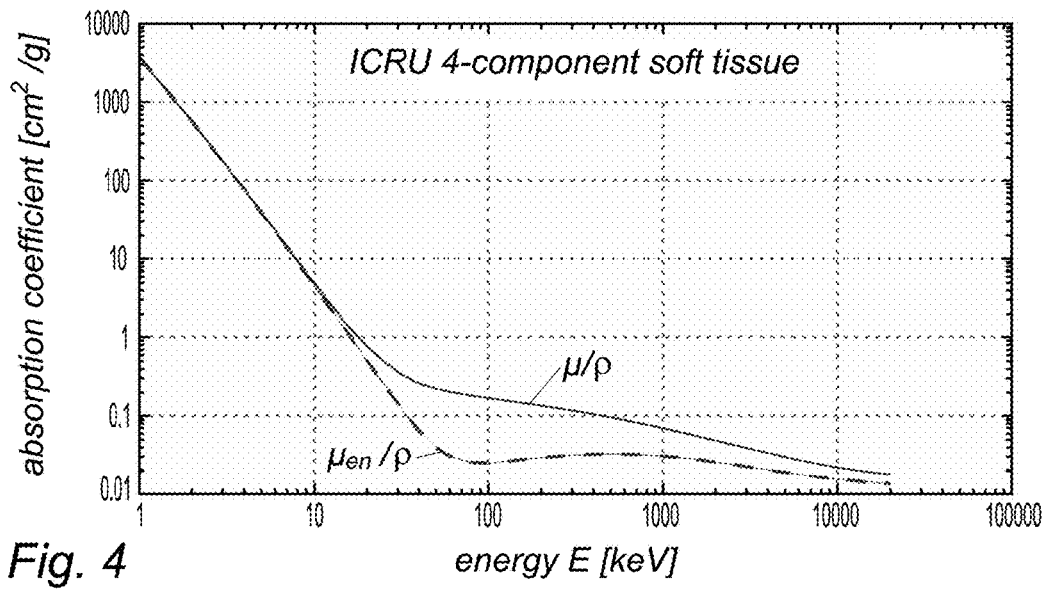
FIG. 4, a plot of the mass absorption coefficient and of the mass energy absorption coefficient for ICRU 4-component soft human tissue as a function of photon energy.

Here, the factor g represents the average fraction of the kinetic energy of secondary charged particles (produced in all the types of interactions) that is subsequently lost in radiative (photon-emitting) energy-loss processes as the particles slow to rest in the medium [Hubbell and Seltzer, 1999]. For details on the calculation of g, see also Hubbell and Seltzer [1999]. Tabulated values for $\mu_{tr}$ and $\mu_{en}$ for ICRU 4-component soft tissue can be found in the same reference. FIG. 4 shows the mass attenuation coefficient $\mu_{en}/\rho$ and the mass energy-absorption coefficient $\mu_{en}/\rho$ for 4-component soft tissue.

Similar to Eq. (20) the absorbed dose D, which is defined as the mean energy $\overline{d}_\in$ imparted by ionizing radiation to a mass dm, can be calculated as:

$$D := \frac{d\overline{e}}{dm} = \int_0^{E_{max}} F_{3,A}(E) \cdot E \cdot \Delta t_A \cdot \frac{\mu_{en}(E)}{\rho} dE + \int_0^{E_{max}} F_{3,B}(E) \cdot E \cdot \Delta t_B \cdot \frac{\mu_{en}(E)}{\rho} dE \quad (22)$$

For medical applications the absorbed dose D is more interesting than the kerma K, but it should be stressed that the inventive approach allows us to compute both quantities.

Furthermore, the information given by $F_{3,P}(E)$, i.e. the energy resolved flux at the tumor level, is of greater value than the integrated dosimetric quantities K and D. This might be useful to further investigate the enhancement of radiosensitization observed in nanoparticle based radiotherapy.

Beside the determination of the absorbed dose, the presented approach also allows measuring the total mass of nanoparticles $m_{np}$ at the tumor position.

Like the kerma and the dose, the mass $m_{np}$ is obtained by two measurements performed in the two different configurations. An average of the two allows minimizing statistical fluctuations:

$$m_{np} = (m_{np,A} + m_{np,B})/2 \quad (23)$$

The total mass $m_{np}$ allows correcting for the, up to now, neglected physical dose enhancement caused by the increased absorption by high-Z nanoparticles. The presented calculations for the kerma and the absorbed dose can be modified by an increased mean absorption coefficient $$\mu_{tr}/\rho = M_{ICRU4} \cdot \mu_{tr_{ICRU4}}/\rho_{ICRU4} + M_{np} \cdot \mu_{tr_{np}}/\rho_{np} \quad (24)$$

$$\mu_{en}/\rho = M_{ICRU4} \cdot \mu_{en_{ICRU4}}/\rho_{ICRU4} + M_{np} \cdot \mu_{en_{np}}/\rho_{np}. \quad (25)$$

where $M_{ICRU4}$ and $M_{np}$ are the mass ratios for soft tumor tissue (with mass $m_{tumor}$) and for the material of the nanoparticles, respectively.

Even if the relative amount of nanoparticles is negligible compared to the soft tissue, the knowledge of $m_{np}$ is an important item of information additional to the absorbed dose D, because the enhancement of radiosensitization by nanoparticles is believed to be caused by additional chemical and biological effects of the irradiated nanoparticles that exceed the physical dose enhancement by far. Cheng et al. [2012] report a chemical enhancement that exceeds the physical expected enhancement by a factor of about 2000. Therefore, the total mass $m_{np}$ not only allows correcting for the neglected physical dose enhancement but is also an important input parameter for chemical and biological models.

As a synthesis, the dose/kerma can be summarized with the following steps:

1. The apparatus is set in its first configuration (A=source, B=detector).
2. $F_{2,A}(E)$ is measured or known.
3. $F_{5,B}(E)$ is measured.
4. $\overline{d}_{abs,B}$ is computed using equation (17).
5. $att_B(E)$ is computed using equation (7).
6. The configuration is inverted, i.e. the apparatus is set in its second configuration (B=source, A=detector).
7. $F_{2,B}(E)$ is measured or known.
8. $F_{5,A}(E)$ is measured.
9. $\overline{d}_{abs,A}$ is computed using equation (17).
10. $att_A(E)$ is computed using equation (7).
11. $F_{3,A}(E)$ and $F_{3,B}(E)$ are computed using equation (3).
12. Optionally, the kerma K is computed using equations (19) and (20).
13. The absorbed dose D is computed using equation (22).

Moreover, if the nanoparticle mass also has to be determined:

14. $F_{4,A}(E)$ and $F_{4,B}(E)$ are computed using equation (5).
15. $m_{np,P}$ is computed using equations (4) and (8).
16. $m_{np}$ is computed using equation (23).

Figure 5:
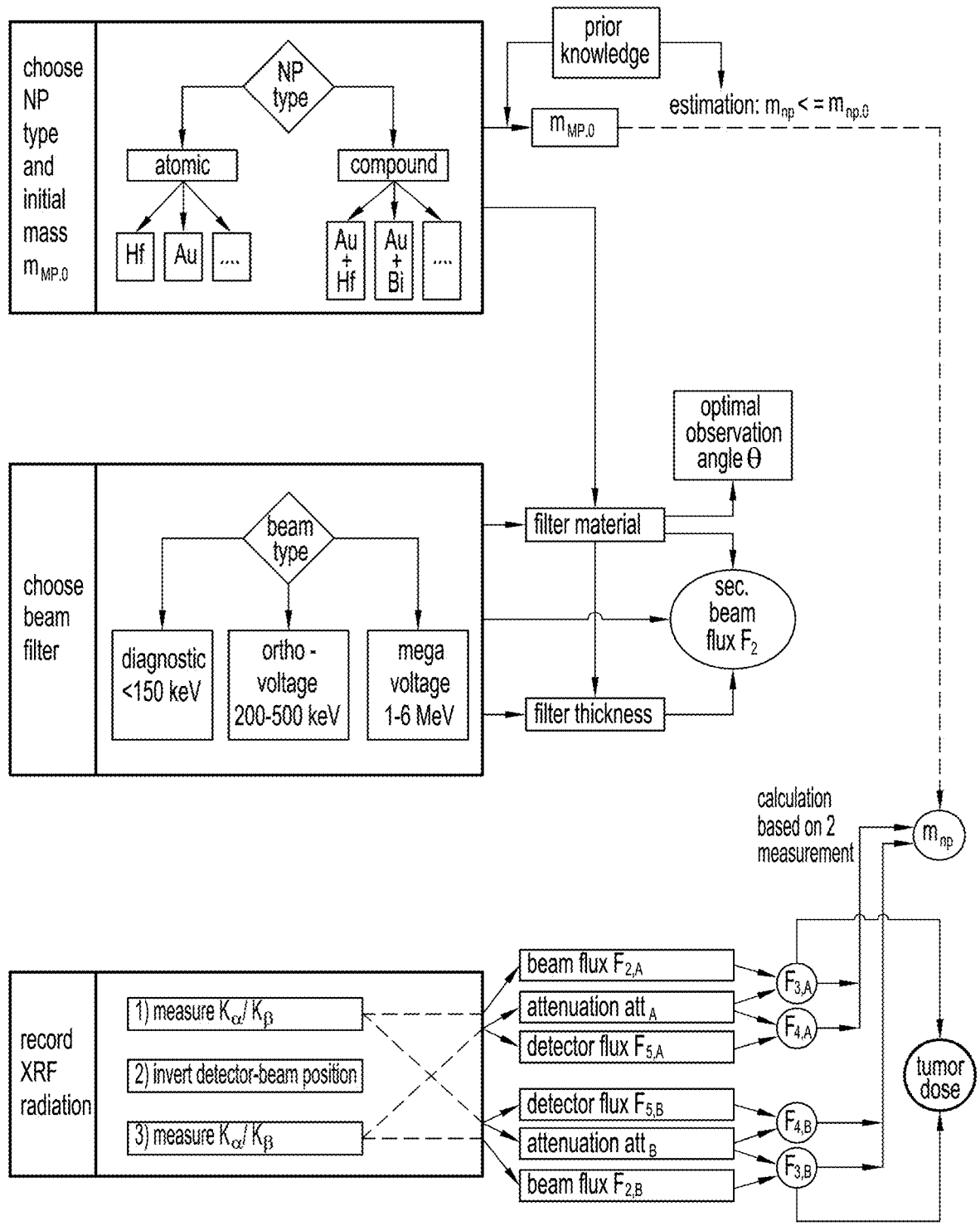
FIG. 5, a schematic overview of a method according to the invention.

FIG. 5 provides an outline of the inventive method.

First of all, the nanoparticle (NP) type is chosen, as well as their estimated mass inside the tumor, $m_{np,0}$. Nanoparticles may be "atomic", i.e. comprising a single heavy metal such as Hf or Au or compound (e.g. Au+Hf, Au+Bi, etc.).

The beam type, and more particularly its tube voltage and therefore maximum energy $E_{max}$ has also to be chosen. In particular, diagnostic ($E_{max}$<150 keV), orthovoltage (200 keV<$E_{max}$<500 keV) or megavoltage (1 MeV<$E_{max}$<6 Mev) may be used. The filter material(s) and thickness are then chosen, also taking into account the choice of nanoparticle material(s). The filter characteristics and the beam type determine the filtered flux $F_2$, which can be either measured or computed.

Moreover, the nanoparticle material(s) and the beam type allow choosing the observation angle θ.

Then the nanoparticle-loaded tumor is irradiated through the filter, XRF radiation is recorded at observation angle θ and the $K_\beta/K_\alpha$ ratio is computed for two symmetrical configurations of the apparatus. This allows computing $F_{3,A}$, $F_{3,B}$, $att_A$, $att_B$, $F_{5,A}$, $F_{5,B}$, which in turn allows computing the dose D received by the tumor and the actual nanoparticle mass $m_{np}$.

The dimensioning of the filter, the choice of the material of which the nanoparticles are made and that of the optimal detection angle θ are important issues for optimizing the sensitivity of the invention. They will be considered in detail in the following.

The idea behind using a filter is to enhance the signal-to-noise ratio of XRF measurements which uses broad band X-ray emitters, such as X-ray tubes, as primary sources. It applies for all kind of X-ray tubes, i.e. diagnostic tubes ($E_{max}$<150 keV), orthovoltage tubes (200 keV<$E_{max}$<500 keV), and mega-voltage tubes ($E_{max}$>1000 keV).

Figures 9A, 9B:
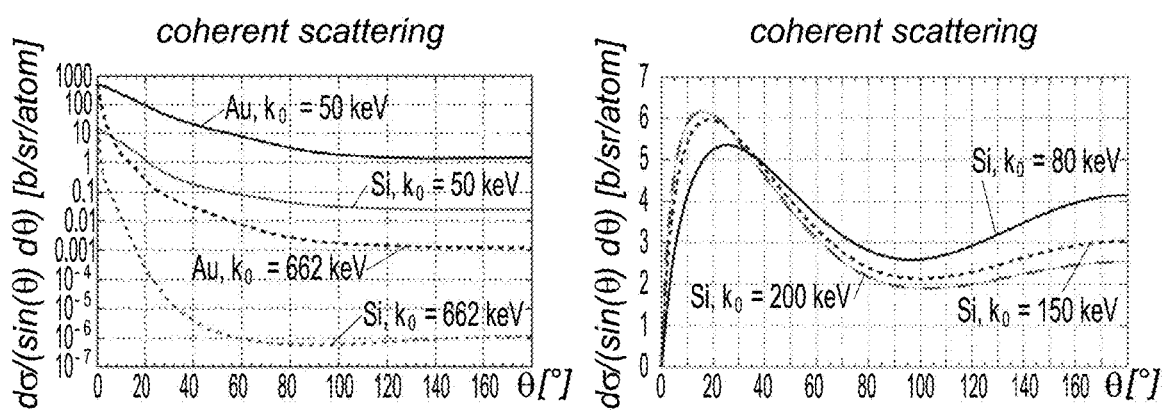
FIGS. 9A and 9B, plots of the X-ray scattering cross-section dσ as a function of the scattering angle θ for Si and Au (9A: coherent scattering; 9B: incoherent scattering)

The filter is used to reduce the undesirable X-ray flux of the beam within a specific energy interval. The combination of this filter with a properly chosen observation angle θ allows reducing the background around the observed XRF lines. The choice of the observation angle θ depends on two independent considerations. First, according to the general properties of coherent and incoherent scattering, θ should be close to 90° in order to reduce the scattered background component, see FIGS. 9A and 9B. This is true for any kind of filter. Second, θ is chosen according to filter specific considerations in order to create an energy window with a reduced background flux at the XRF energy. Finally, the two considerations must result in a compromise for θ. This can be done by choosing the filter material in a way that the optimal angle for filtering (see FIG. 13) results in θ close to 90°.

For XRF measurements, a filter that reduces the background radiation at the energy of the XRF lines is highly desirable as it increases the signal-to-noise ratio of the measurement. This is especially true for setup configurations with a large background radiation that results from scattered photons of the primary beam.

The XRF lines of a target material are produced by the integrated flux above the corresponding absorption edge of the target material. The absorption edge of an element is always at higher energies than the respective XRF lines. Therefore, an ideal filter would filter out all X-rays with an energy below the absorption edge of the target material and pass all X-rays with higher energies (see FIG. 8C). In this way, the XRF lines could be detected within a low background.

Unfortunately, such a filter with a sharp rising edge in its transmittance for increasing energies cannot be produced. The reversed effect, i.e. a sharp falling edge of the transmittance of a material for increasing energies, is realized by the photoelectric absorption at the corresponding absorption edge, see FIG. 8B, wherein the continuous line corresponds to a "thick" filter and the dashed one to a "thin" one. The position of the absorption edge depends on the filter material but the general shape of the transmittance curve around the absorption edge (i.e. the step downwards followed by a slight increase for higher energies) is independent of the type of material. The filter thickness defines the depth of the step of the transmittance curve at the absorption edge.

Figures 8A, 8B, 8C:
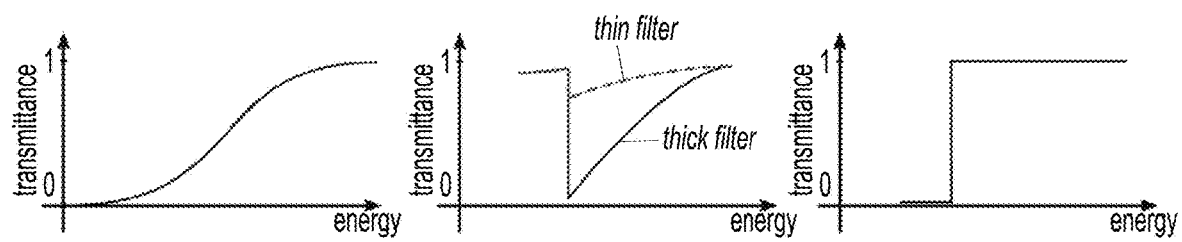
FIGS. 8A, 8B and 8C, simplified plots of the X-ray transmittances of different sorts of X-ray filters.

FIG. 8A corresponds to an X-ray filter without absorption edges, whose transmittance gently increases with photon energy.

The principal idea is to shape the primary X-ray beam in a way that it has an energy interval with a reduced flux. This region of reduced background is then shifted to the position of the XRF lines by incoherent scattering.

In the typical energy range of the primary X-ray beam (several tens to hundreds of keV), the dominant photon interactions with the target material are coherent scattering, incoherent scattering (often misnamed as Compton scattering), and photoelectric absorption. The observation angle for the XRF detection is typically chosen θ>0° in order to be "out of the beam" in a low background environment. Therefore, only coherent and incoherent scattering contribute to the background radiation and photoelectric absorption can be neglected for the following discussion. Furthermore, the discussion is limited to the case of unpolarized X-rays, as this is the usual case for the primary radiation.

In most cases, a minimal cross section is reached for scattering angles θ≥90°.

The atomic number of the filter material $Z_{filter}$ and the atomic number of the target material $Z_{target}$ are related by:

$$Z_{filter} = Z_{target} + n. \quad (26)$$

Three cases must be distinguished:

n<<0: If the atomic number of the filter material is much lower than the one of the target material the target XRF lines are positioned on the right side of the K-edge of the filter, see FIG. 10A. In this case the XRF lines are positioned within a low background.

n≤0: If the atomic number of the filter material is only slightly lower than the one of the target material the XRF lines are positioned on the left side of the K-edge of the filter, see 10B. In this case the XRF lines are positioned within a high background and an increased signal-to-noise ratio can only be achieved for observation angles θ>0°, see below.

n>0: If the atomic number of the filter material is larger than the one of the target material the XRF lines are positioned on the left side of the K-edge of the filter, see 10C. In this case the XRF lines are positioned within a high background and an increased signal-to-noise ratio can only be achieved for observation angles θ>>0°, see next section. Compared to the case n≤0, this scenario has the advantage that a fraction of the primary photons—those with energies $K_{edge,target}$<E<$K_{edge,filter}$—are only slightly attenuated and can contribute to the XRF signal generation. Because these photons are close to the K-edge of the target material, they have a large cross section for photoelectric absorption by the target; i.e. they produce a strong XRF signal.

Figure 11:
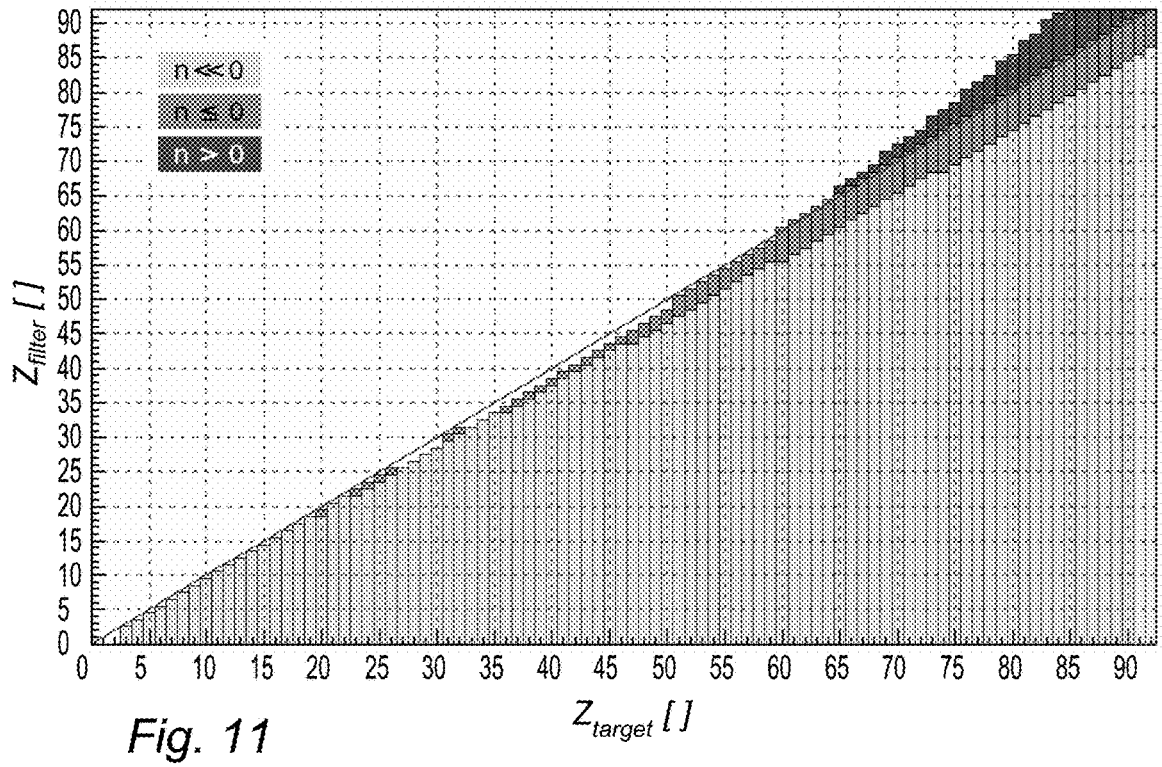
FIG. 11, a plot identifying different kinds of target/filter combinations.

The energy difference between the K-edge and the XRF lines depends on the atomic number Z. Furthermore, the energy loss by incoherent scattering is itself a function of the energy. Therefore, not all of the three cases presented above are possible for each target material. FIG. 11 summarizes what combination of filter and target material results in which of the above mentioned cases for the example of the $K_{\alpha 1}$ XRF line.

Figure 12:
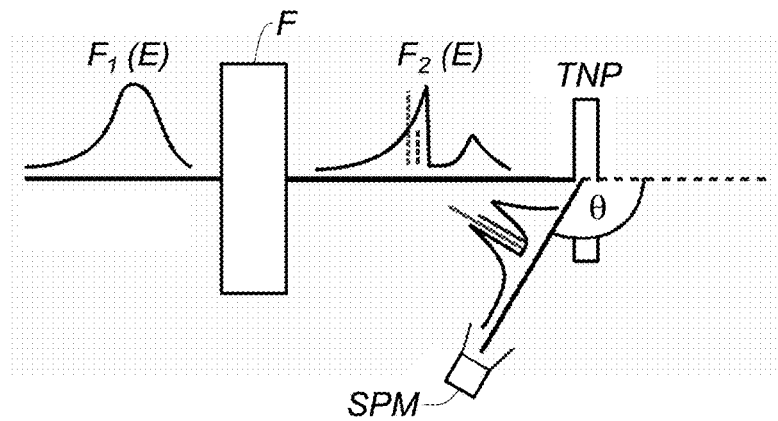
FIG. 12, a schematic view of the geometry of X-ray fluorescence excitation and detection according to the invention.

Observing the XRF under an observation angle θ (see FIG. 12) shifts the background radiation to lower energies while the XRF radiation remains at its specific line energy. For the case n<<0, the XRF lines are already positioned in a low background environment and any scattering angle θ>0° shifts this low background environment further away from the XRF lines. This argument should not be mixed up with the fact that the overall background is reduced for scattering angles θ≈90°, as illustrated on FIGS. 9A and 9B.

For the cases n≤0 and n>0, a proper selection of the observation angle θ allows shifting the low flux component of the primary beam to the XRF lines which enhances the signal-to-noise ratio. The energy of the scattered photons $E_{sc}$ (with initial energy E) can be calculated according to.

$$E^{sc} = \frac{E}{1 + \frac{E}{511 \text{ keV}}(1 - \cos(\theta))} \quad (27)$$

Figure 13:
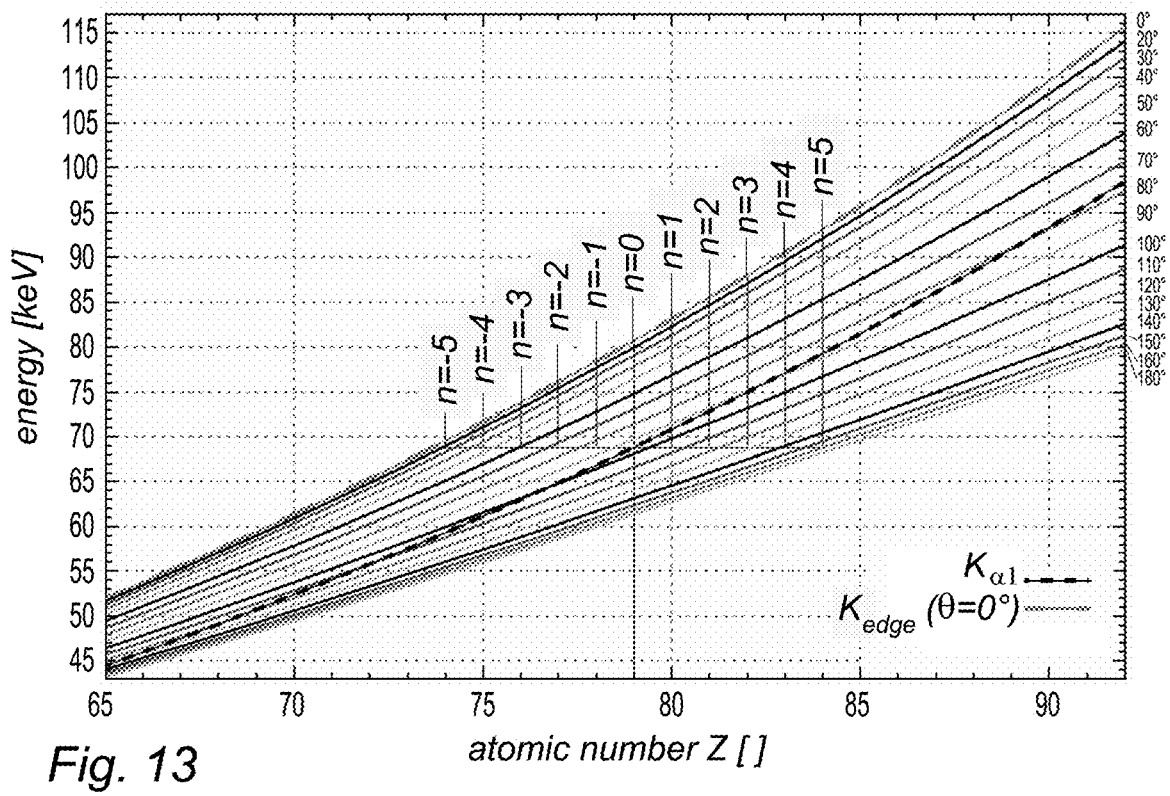
FIG. 13, plots of shifted beam energies at the position of the $K_{\alpha 1}$ fluorescence line as a function of atomic number and for different scattering angles.

See FIG. 13 for computed values for the energy shift for different scattering angles.

Figure 14:
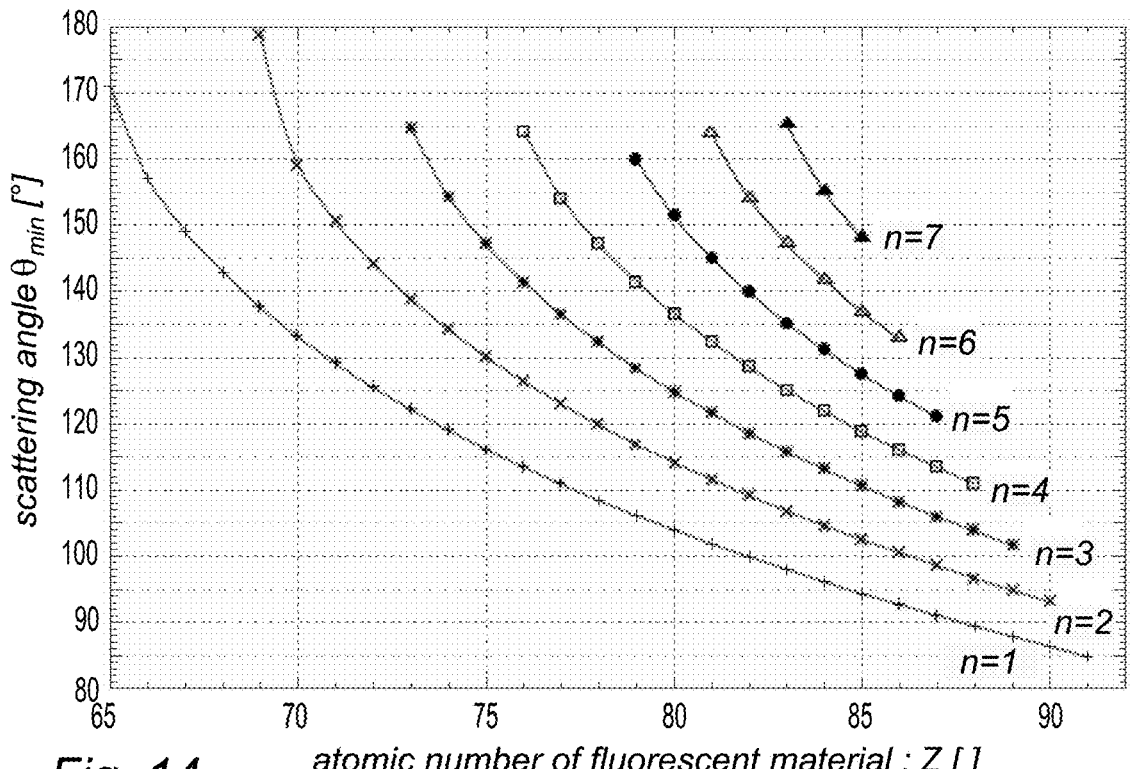
FIGS. 14 and 15, plots of minimal scattering angles θmin as functions of atomic number and for different filter materials.
Figure 15:
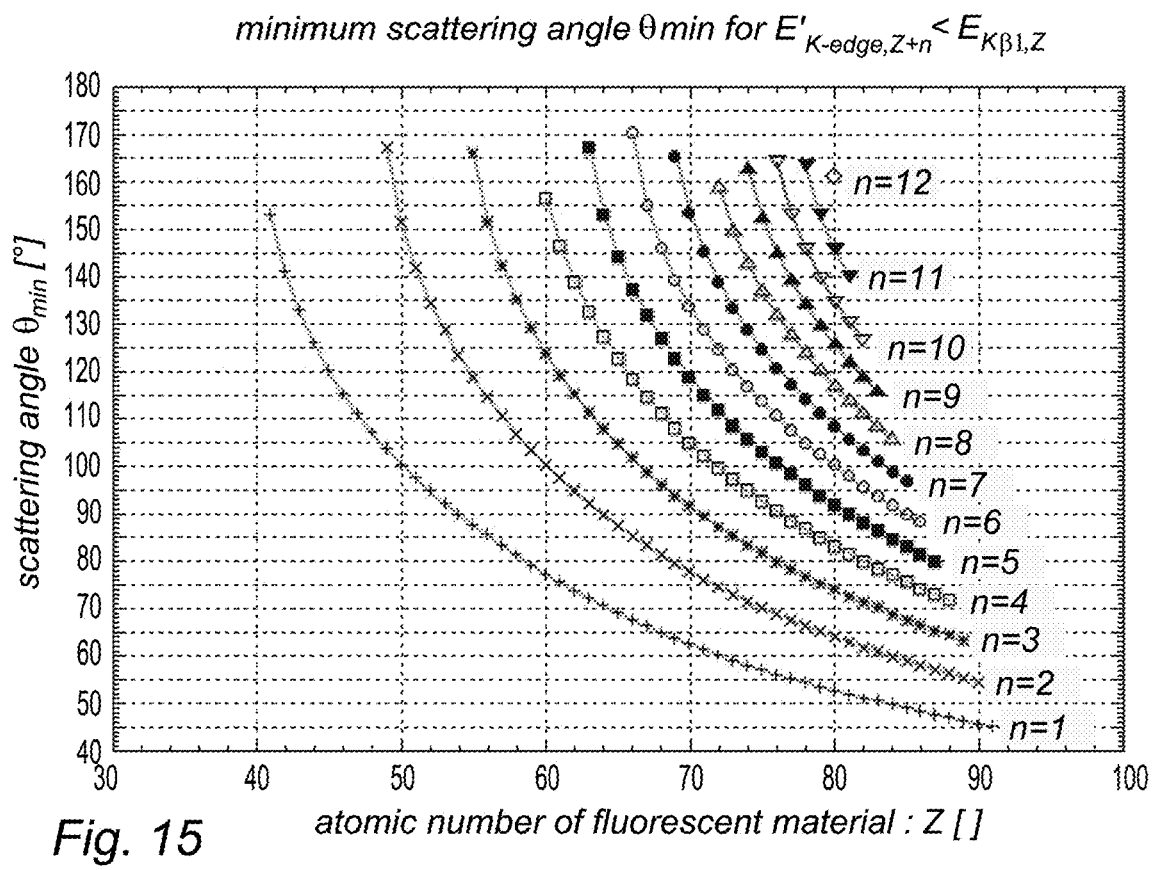

The case n>0 can only be applied if the energy difference between the fluorescence line and the absorption edge of the filter is smaller than the maximal energy loss caused by incoherent scattering (i.e. for 180° back scattering). For the $K_{\alpha 1}$ line (which is the dominant XRF line) this condition can be reached for target materials with $Z_{target} \geq 65$, see FIG. 11 and FIG. 14, while for the more energetic $K_{\beta 1}$ line $Z_{target} \geq 41$ is required, see FIG. 15. For other fluorescence lines the minimal required atomic number of the target $Z_{target,min}$ to reach the case n>0 are listed in Table 1.

TABLE 1

| Siegbahn notation | IUPAC notation | $Z_{target,\ min}$ for n > 0 |
|---|---|---|
| $K_{\alpha 1}$ | K-L3 | 65 |
| $K_{\alpha 2}$ | K-L2 | 68 |
| $K_{\beta 1}$ | K-M3 | 41 |
| $K_{\beta 2}$ | K-N2 and K-N3 | 37 |
| $K_{\beta 3}$ | K-M2 | like $K_{\beta 1}$ |
| $L_{\alpha 1}$ | L3-M5 | not possible |
| $L_{\alpha 2}$ | L3-M4 | not possible |
| $L_{\beta 1}$ | L2-M4 | not possible |
| $L_{\beta 2}$ | L3-N5 | not possible |
| $L_{\gamma 1}$ | L2-N4 | 85 |
| $M_{\alpha 1}$ | M5-N7 | not possible |

In the following calculation the filter thickness is chosen in a way to maximize the signal-to-noise ratio of the $K_{\alpha 1}$ fluorescence line. The calculations for other fluorescence lines can be done in an equivalent way.

For a given primary photon flux $F_1(E|E_{max})$ and a given filter (with thickness d and attenuation coefficient $\mu(E)$) the secondary flux $F_2(E|E_{max})$ that exits the filter can be calculated according to:

$$F_2(E|E_{max}) = F_1(E|E_{max}) \cdot e^{-\mu(E)d} \quad (28)$$

The following calculations use a theoretic model (Hernandez and Boone [2014]) for the outgoing tube flux $F_1(E|E_{max})$. The intensity of this flux—which can be set by the tube current—is of no further interest for the calculation of the signal-to-noise ratio (SNR), but only the spectral shape. Therefore, all of the input spectra are normalized in a way that their maximum is set to 1.

The flux $F_2$ is slightly modified by human tissue absorption. While the associated total flux reduction cannot be neglected for an accurate dose calculation, it is of no interest for the SNR calculation due to the normalization. The reshaping of the spectra by the human tissue is of importance, but it is considered to be small compared to the reshaping effect of the filter. Therefore, for the filter thickness optimization, $F_2(E) \approx F_3(E)$ is assumed. The flux at the tumor level $F_3(E)$ is contributing to the signal and to the noise generation in different ways so that an optimal filter thickness can be estimated.

The fluorescence signal S results from all photons with an energy above the K-edge of the target EK weighted with the probability for photoelectric absorption $\sigma_{PE}(E)$:

Here the question arises in what way the maximal tube energy Emax influences the signal generation. To answer this, it is helpful to compute the cross section for the photoelectric effect normalized to its maximal value at the absorption edge:

$$\sigma_{PE}^*(E) = \frac{\sigma_{PE}(E)}{\sigma_{PE}(E_K)} \quad (29)$$

The cumulative distribution of $\sigma^*_{PE}(E)$ is then calculated as:

$$CDF_{PE}(E) = \frac{\int_0^E \sigma_{PE}^*(E')dE'}{\int_0^\infty \sigma_{PE}^*(E')dE'} \quad (30)$$

Figure 16A:
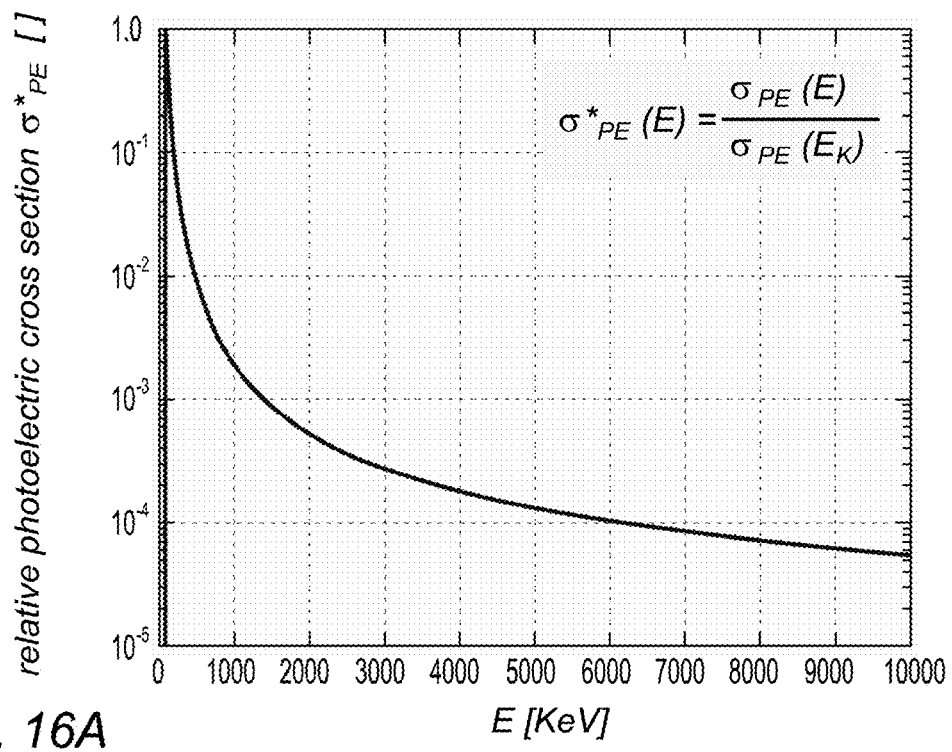
FIGS. 16A and 16B, respectively, the normalized photoelectric cross section and normalized cumulative photoelectric cross section of gold.
Figure 16B:
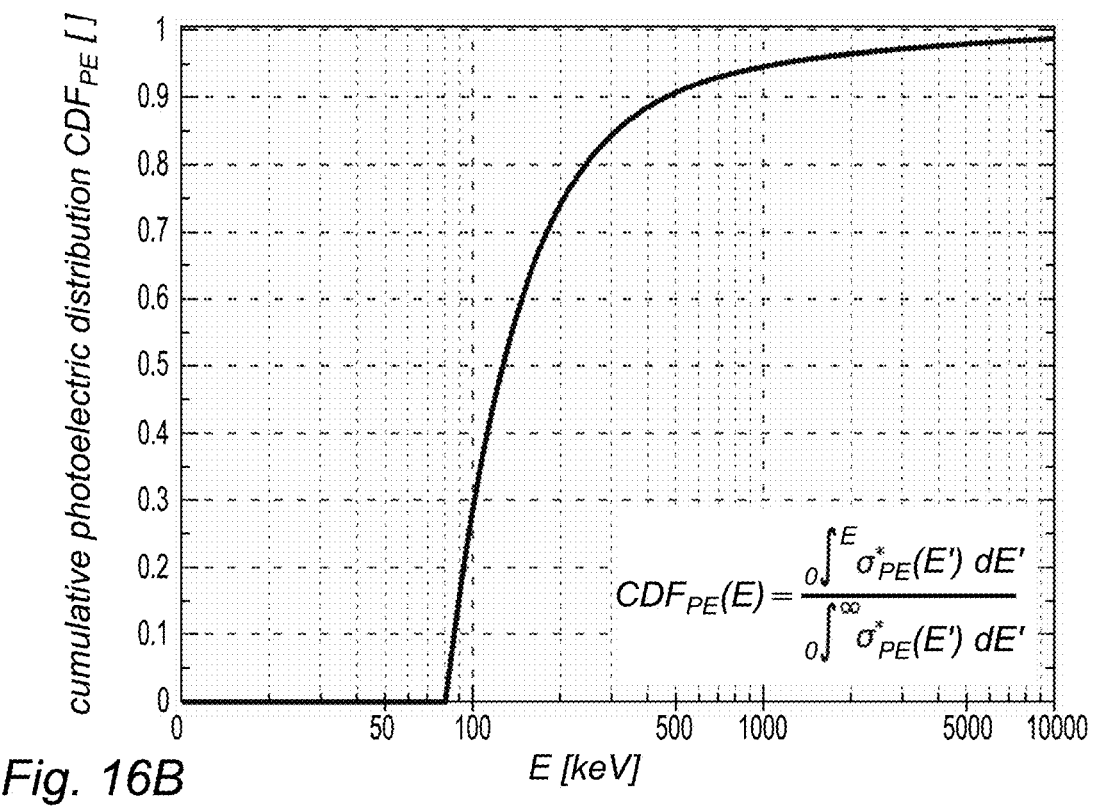

FIGS. 16A and 16B, respectively, show the normalized cross section and the cumulative photoelectric distribution $CDF_{PE}$ for the photoelectric effect in gold. In order to get a strong fluorescence signal the maximal tube energy should be in the range of several 100 keV. Above several MeV the signal generation saturates and is close to its maximal value. For reasons of simplicity the parameter $E_{max}$ is no longer listed explicitly in the following equations.

In order to combine the effect of photoelectric absorption with a realistic tube spectrum, the signal function S(E) and the total signal S are computed as follows:

$$S(E) = F_3(E) \cdot \sigma_{PE}^*(E) \quad (31)$$

$$S = \int_{E_K}^{E_{max}} S(E)dE \quad (32)$$

$$CDF_S(E) = \frac{1}{S} \cdot \int_{E_K}^{E} S(E')dE' \quad (33)$$

Figure 17A:
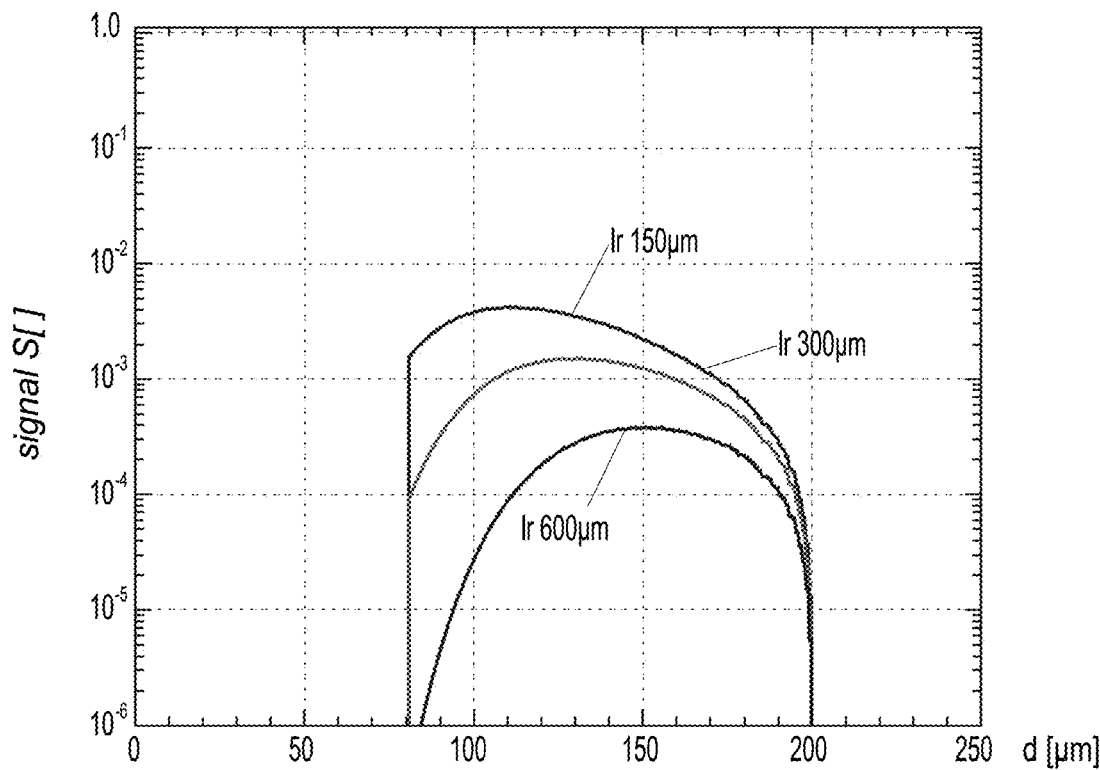
FIGS. 17A and 17B, respectively, plots of the X-ray fluorescence signal of gold and its cumulative distribution function for iridium filters of three different thicknesses.
Figure 17B:
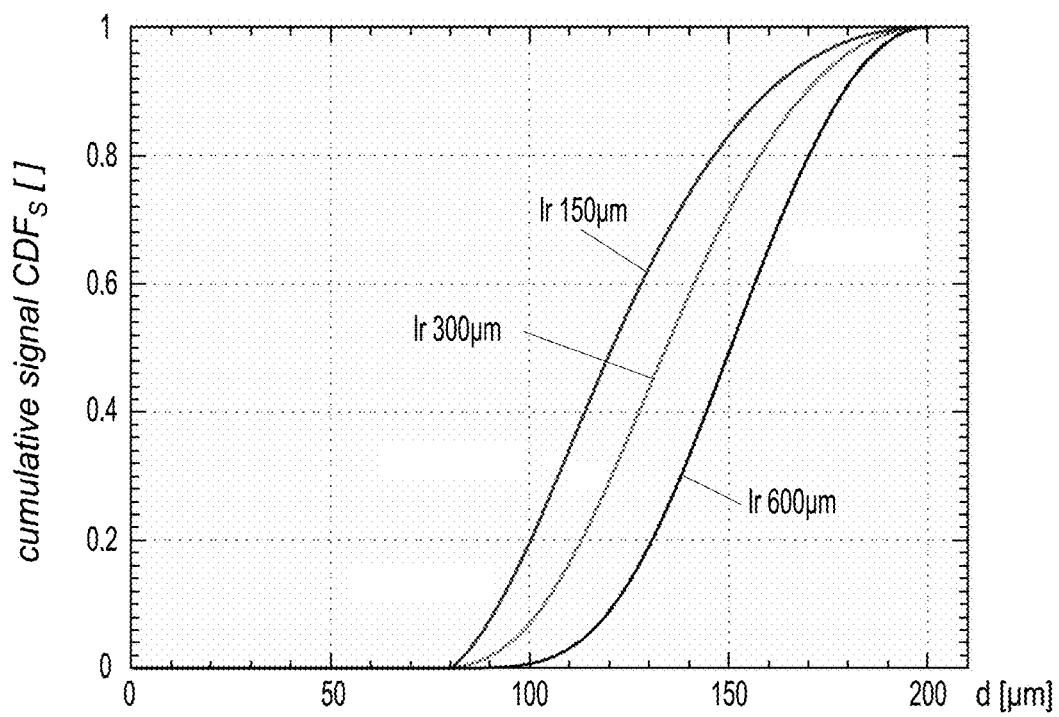
Figure 17C:
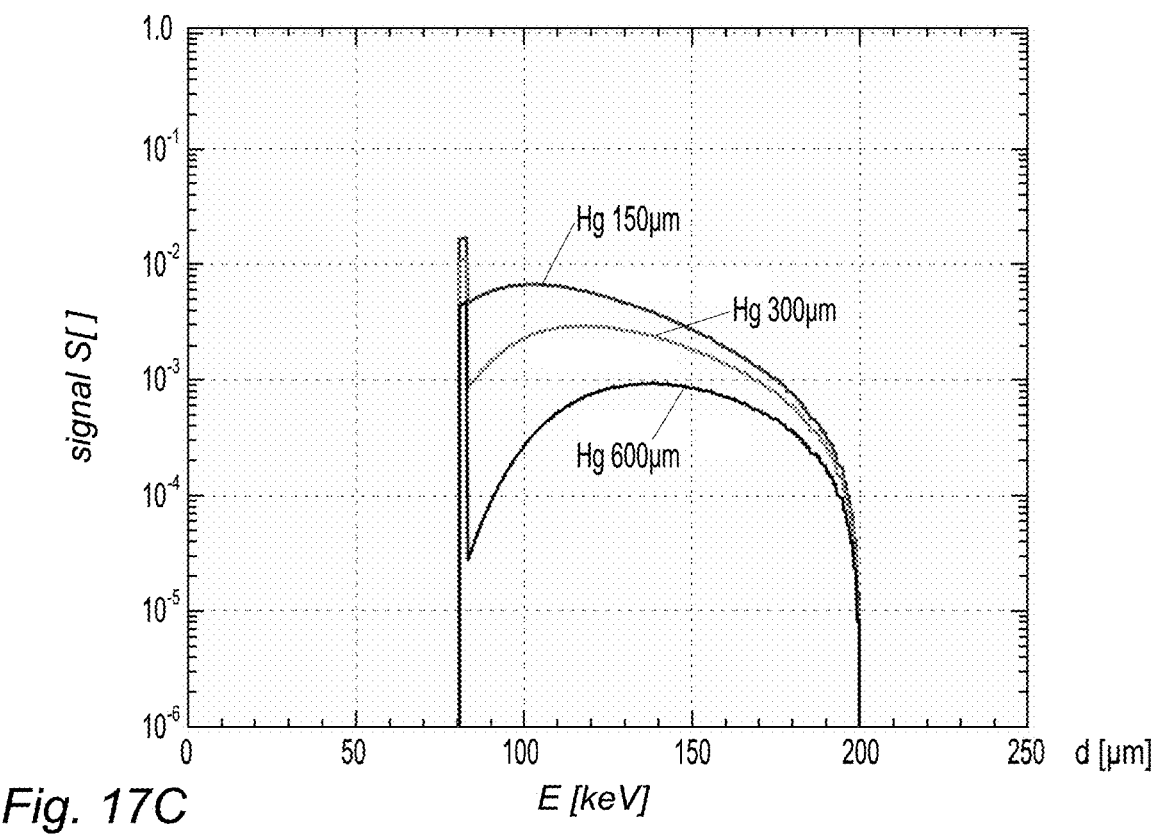
FIGS. 17C and 17D, analogous plots for mercury filters; each plot assumes an X-ray tube spectrum with a tube voltage of 200 kV.
Figure 17D:
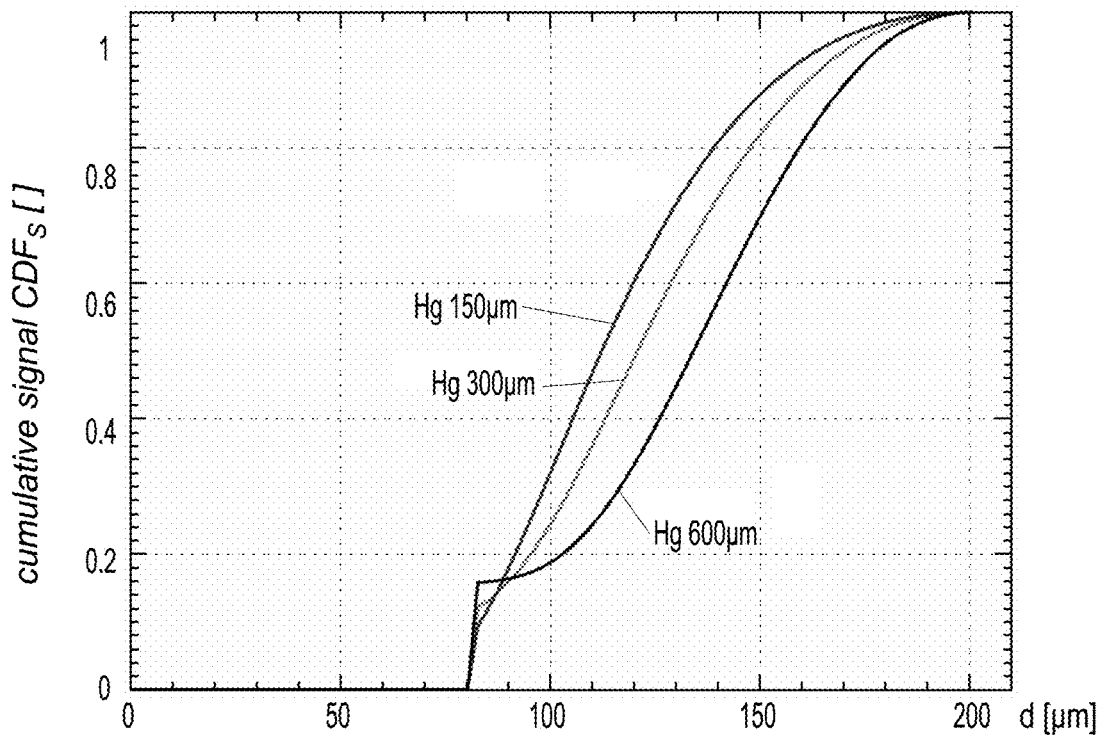

The cumulative distribution function CDFS(E) shows how the signal accumulates with energy and is for illustrative purposes only. FIGS. 17A-D show the signal function and its CDF for a gold XRF measurement using different iridium (n=−2) and mercury (n=+1) filters with $E_{max}$=200 keV. More precisely FIG. 17A is a plot of the XRF signal as a function of depth for an iridium filter of 150 μm, 300 μm and 600 μm, and FIG. 17B is the corresponding CDF. FIGS. 17C and 17D correspond to a mercury filter.

All calculations are performed by a numerical integration using a 500 eV binning and $E_{max}$=200 keV.

The mercury filter (n=+1) clearly shows an enhanced signal generation between the K-edge of gold (~80 keV) and the K-edge of Hg (~83 keV). The thicker the filter the more prominent is this effect.

The noise rate N affecting the XRF signal is proportional to the number of photons per unit time within an interval $\Delta E^{sc}$ around the fluorescence line in the scattered spectrum (with flux $F_4$); this interval is, in the following, called the fluorescence interval. Instead of calculating the spectrum of the scattered flux $F_4$, it is also possible to calculate the noise rate N by shifting the fluorescence interval to the unscattered spectrum (with flux $F_3$). $\Delta E^{unsc}$ is named in the following as noise interval:

$$\Delta E^{unsc} = [E1, E2] \quad (34)$$

$$E_1 = \frac{K_{\alpha 1} - \Delta E/2}{1 - \frac{K_{\alpha 1} - \Delta E/2}{511 \text{ keV}}(1 - \cos(\theta))} \quad (35)$$

$$E_2 = \frac{K_{\alpha 1} + \Delta E/2}{1 - \frac{K_{\alpha 1} + \Delta E/2}{511 \text{ keV}}(1 - \cos(\theta))} \quad (36)$$

$$N \propto \int_{E_1}^{E_2} F_3(E) dE \quad (37)$$

In the following example for a gold XRF detection of $K\alpha 1$ with $\Delta E=4$ keV at $\theta=130°$, the fluorescence interval $\Delta E^{sc}=[66, 70]$ keV in the scattered spectrum becomes a noise interval $\Delta E^{unsc}=[83.8, 90.3]$ keV in the unscattered spectrum.

Figure 18A:
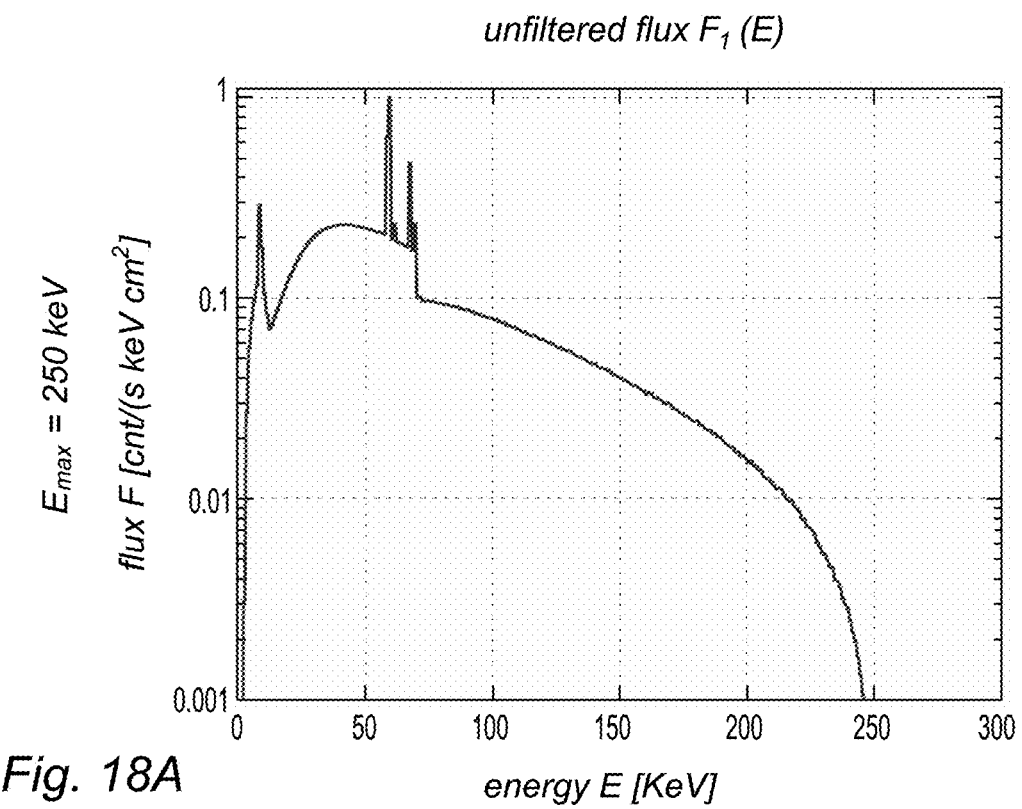
FIG. 18A, the X-ray spectrum of a tube with a tube voltage of 250 kV.
Figure 18B:
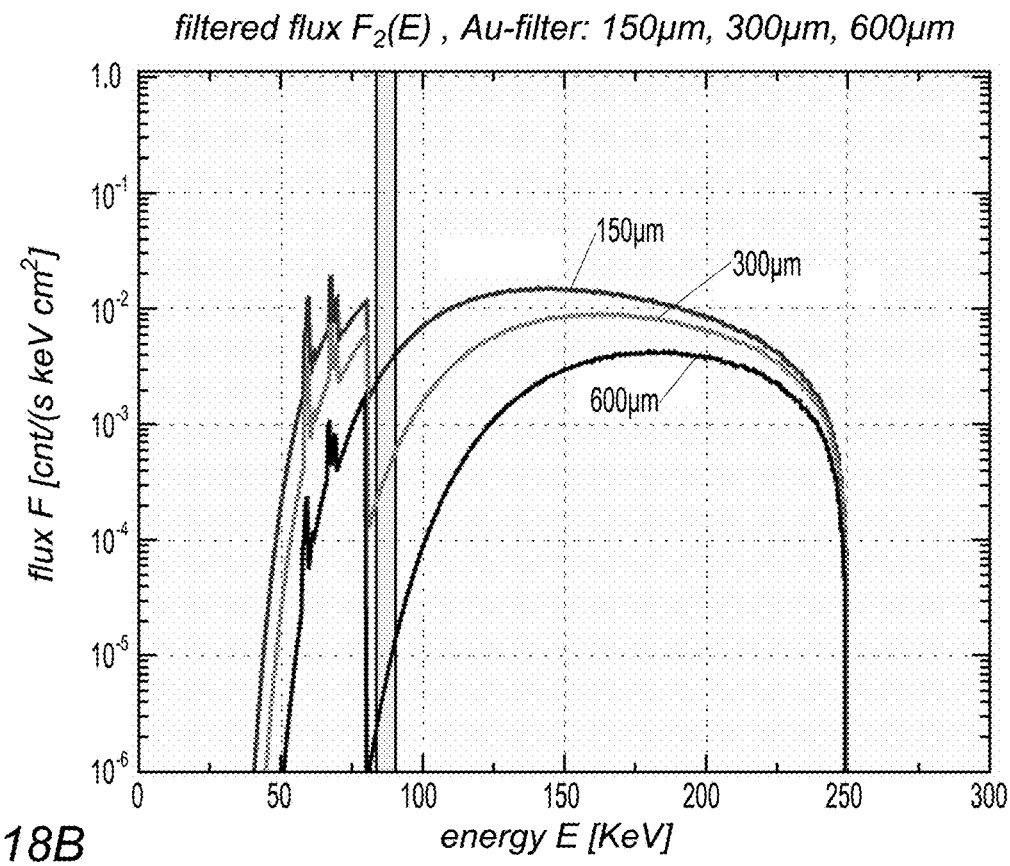
FIG. 18B, the same spectrum after filtering (Au filters of three different thicknesses are considered)
Figure 18C:
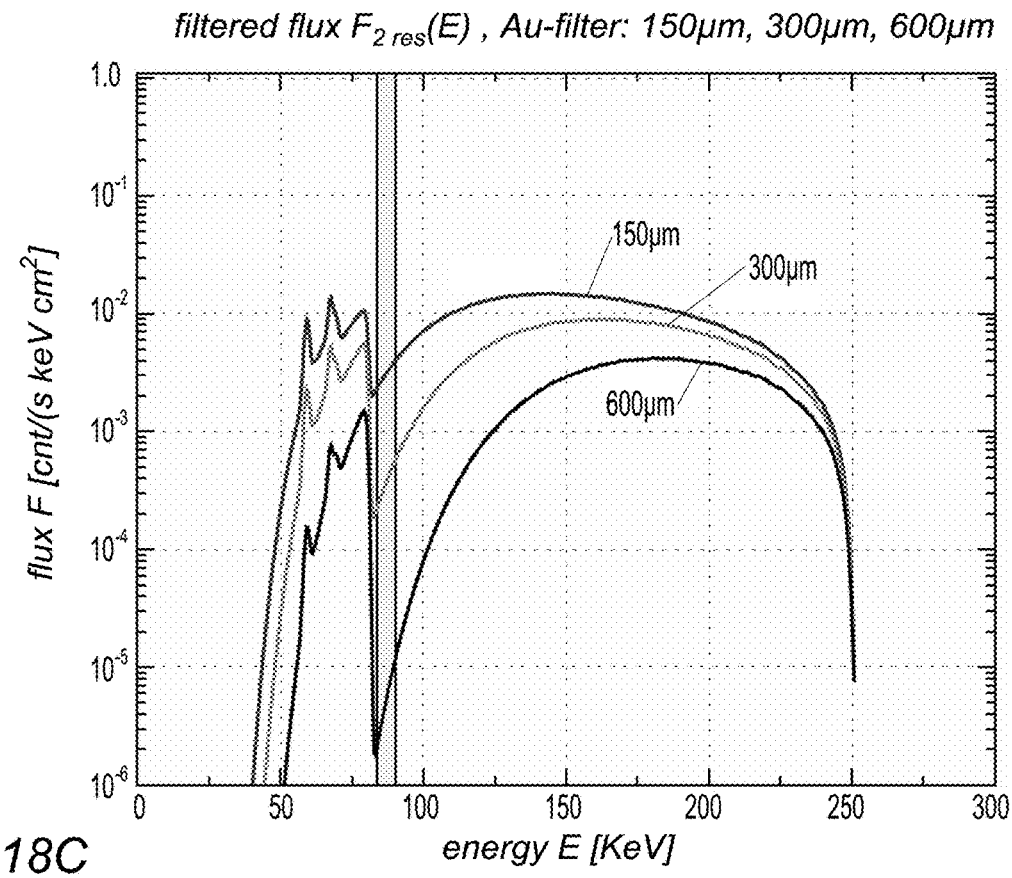
FIG. 18C the same spectra as acquired by a spectrometer with an energy resolution of 1.5 key.

In order to calculate the noise intensity, the spectrum must be modified according to the detector resolution which is assumed to be Gaussian:

$$F_{3res}(E) = F_3(E) * \text{Gauss}(E|\text{resolution}) \quad (38)$$

where "*" represents convolution. This is necessary as the steep falling K-edge of the filter is smoothed by the detector resolution and the detected flux on the right sight of the K-edge (i.e. a part of the noise interval) is enhanced. FIG. 18A shows the unfiltered tube spectrum $F_1(E)$ for $E_{max}=250$ key; FIG. 18B, the filtered fluxes $F_2(E)$ for a 150 µm, 300 µm and a 600 µm gold filter, and FIG. 18C the fluxes of FIG. 18C convoluted by a constant detector resolution $\Delta E=1.5$ keV (full width at half maximum).

With this model the signal-to-noise ratio is always getting better the thicker the filter is chosen. The reason for this can be seen on FIGS. 18B and 18C: the noise is integrated over a small interval which is strongly reduced in its intensity for thick filters while the signal constitutes also partly from photons with higher energies that are less attenuated. Unfortunately, this scenario is not true because the noise flux within the noise interval will saturate to a minimal level even for very thick filters. The effect that the noise is not reduced according to the expected filter attenuation is caused by:

multiple scattering inside the filter: probable because of high flux;

multiple scattering in the sample: probable because of large volume (in the centimeter range);

scattering effects in the detector or in the detector housing: probable because only single scattering is required for this effect.

The true noise contribution can only be evaluated with an accurate simulation of the total setup (tube, filter, sample, camera, detector) which is out of the scope of this estimation. But because the noise contribution is only of interest within a small interval, the noise contribution within the noise interval can be approximated by adding an additional constant (i.e. a noise component independent of the filter; this component can be energy-dependent, but its spectral shape is of no interest as only a relative small spectral region of it adds to the total noise) minimal noise flux $N_c$. So, Eq. (37) becomes:

$$N \propto \int_{E_1}^{E_2} F_3(E) dE + N_c \quad (39)$$

The following calculation investigates the effect of such a minimal noise flux on the SNR while an estimation of this minimal noise flux is given later.

Figure 19A:
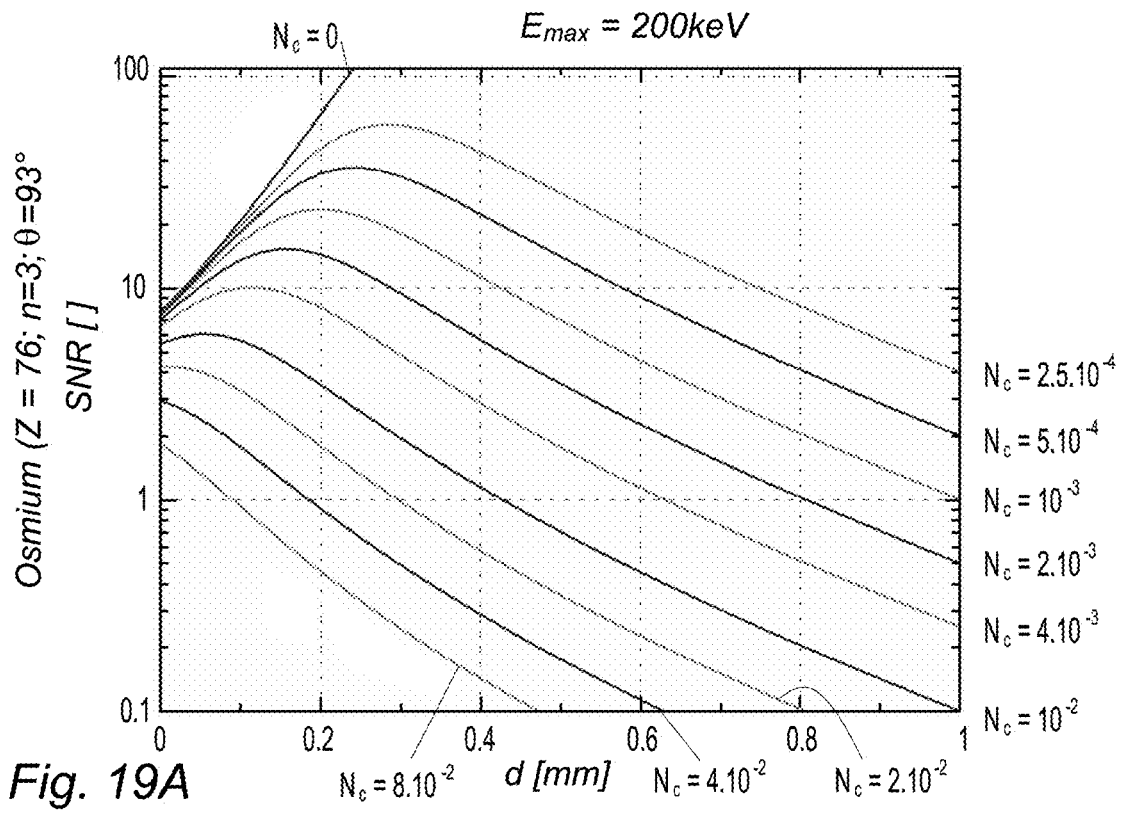
FIGS. 19A, 19B and 19C, plots of the signal-to-noise ratio (SNR) for X-ray fluorescence of gold using osmium filters of different thickness as a function of depth for a tube voltage of 200 keV (19A), 300 keV (19B) and 640 keV (19C)
Figure 19B:
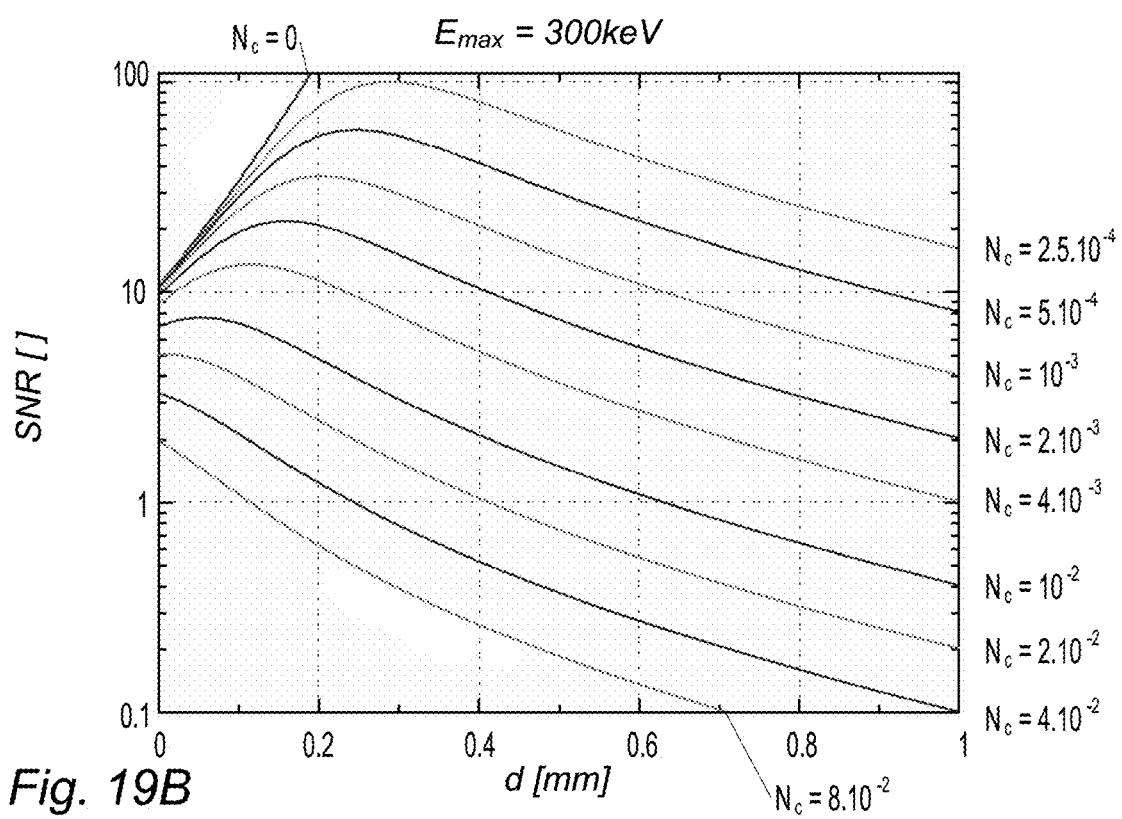
Figure 19C:
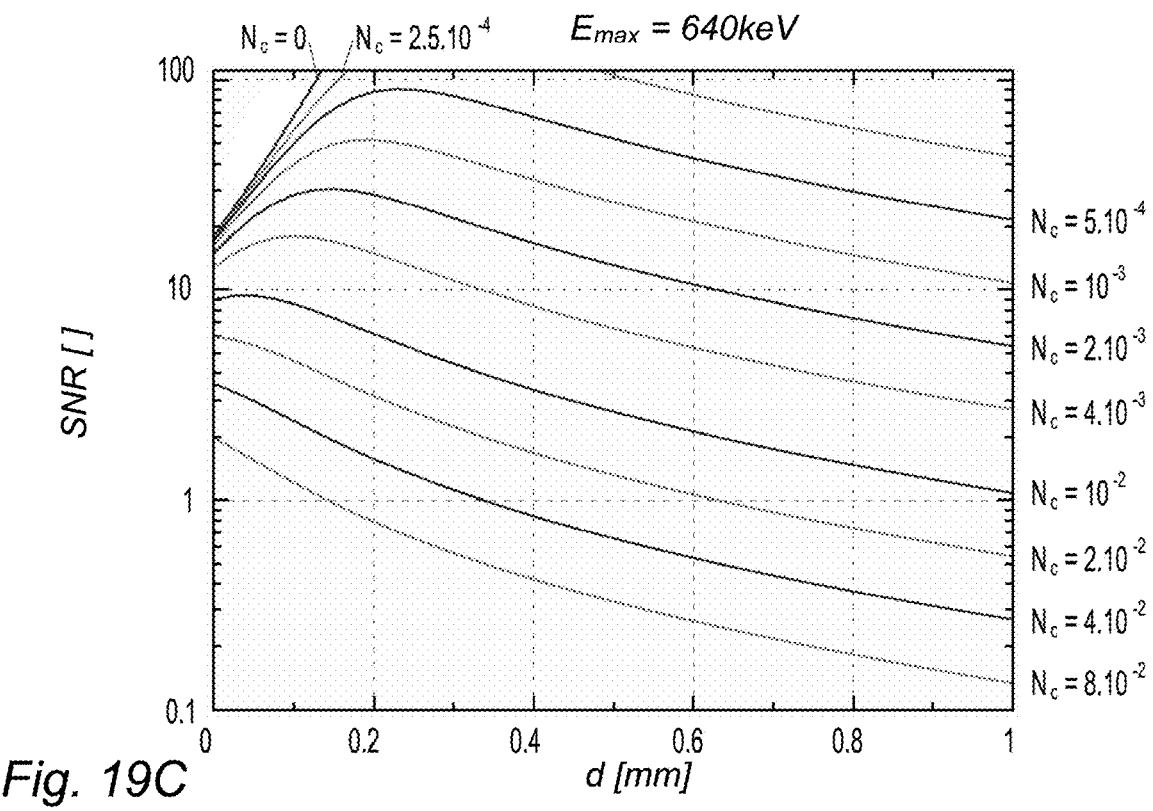

The calculated signal-to-noise ratios are shown on FIGS. 19A to 19C for different $N_c$ values, considering an Osmium filter ($Z=76$, $n=-3$) and an optimum scattering angle $\theta=93°$. FIG. 19A corresponds to $E_{max}=200$ keV, FIG. 19B to $E_{max}=300$ keV and FIG. 19C to $E_{max}=640$ keV.

It can be checked that an accurate knowledge about the constant noise flux is essential for a proper choice of the filter thickness:

without a filter (d=0) the SNR is better the smaller Nc.

For d>0, the SNR gets better for low background levels and worse for high constant noise levels. Indeed, if $N_c$ is large the noise cannot be reduced with a filter; but the signal is reduced by filtering.

The threshold constant noise level for which filtering reduces the SNR is relatively independent of $E_{max}$. Similar calculations performed for Iridium, Gold and Mercury filters shows that it is also relative independent of the filter material. Its value is of the order of 0.02.

Using X-ray tubes with higher accelerating voltages results in a better SNR (with filter and without filter); this is especially true for low constant noise values.

The optimal filter thickness is independent of the tube voltage

Figure 20A:
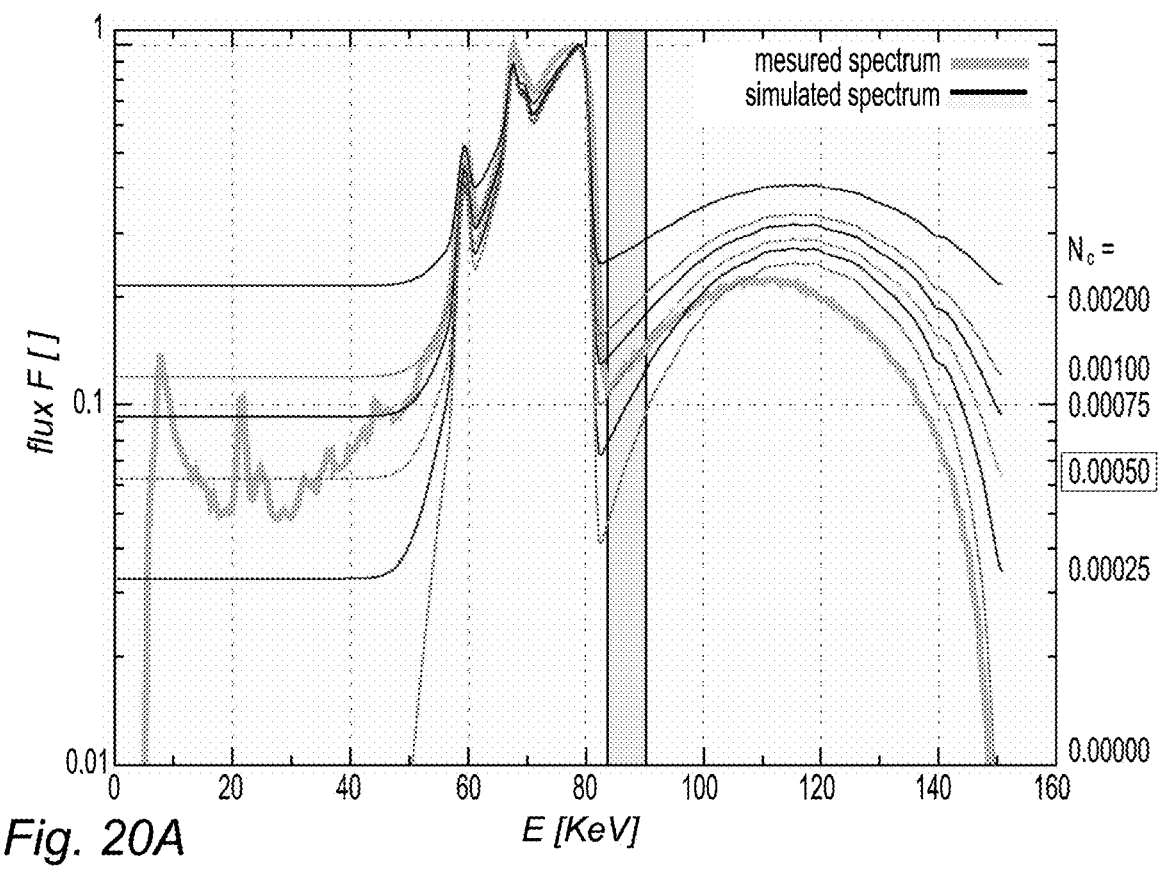
FIGS. 20A and 20B, plots comparing acquired and simulated spectra.
Figure 20B:
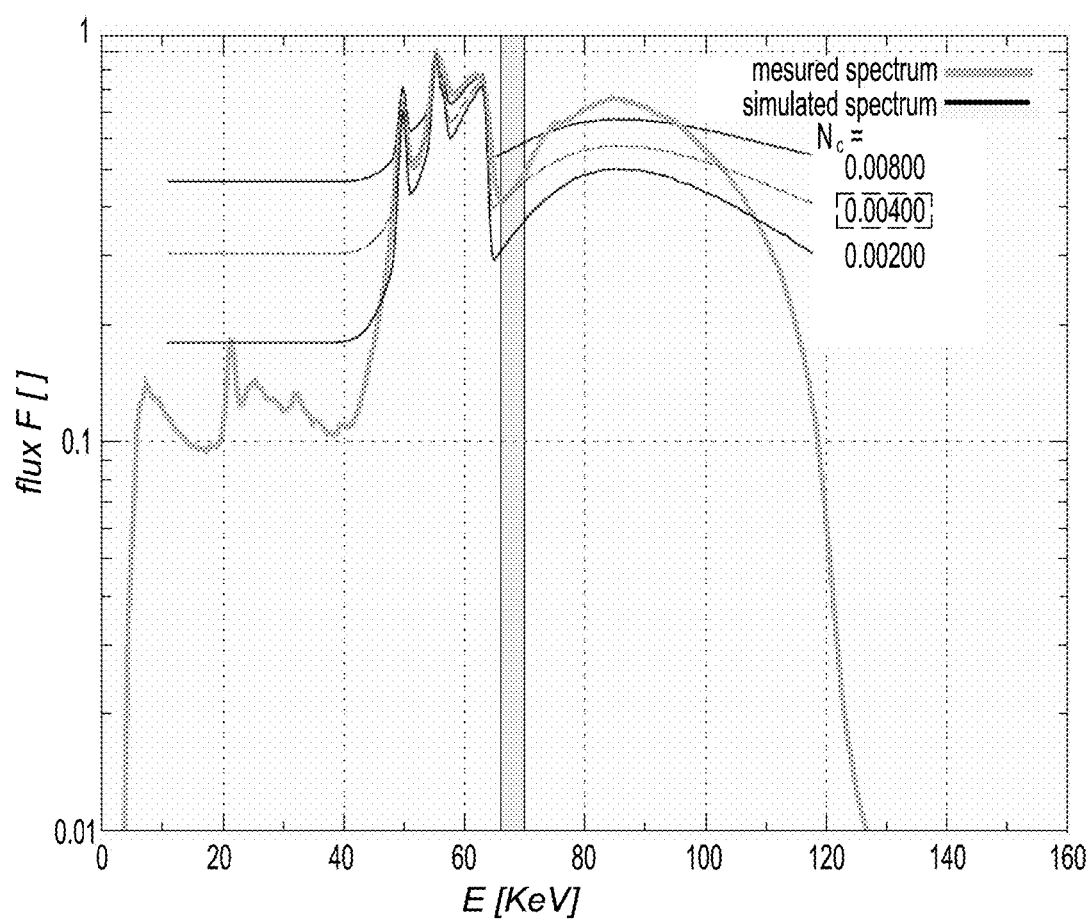

The question how to transform the dimensionless constant noise value to a real flux and which value applies for the experiment can be answered by comparing the calculated spectrum with a measured one. FIGS. 20A-B show a direct ($\theta=0°$—FIG. 20A) and a scattered ($\theta=130°$—FIG. 20B) beam spectrum. The acceleration voltage is 150 kV ($E_{max}=150$ keV) and the filter is composed by 275 µm Au+2 mm Cu+2 mm Al. The different curves correspond to simulations obtained using different noise values $N_c$ (0, $2.5 \cdot 10^{-4}$, $5 \cdot 10^{-4}$, $7.5 \cdot 10^{-4}$, $1 \cdot 10^{-3}$, $2 \cdot 10^{-3}$ for FIG. 20A; $2 \cdot 10^{-3}$, $4 \cdot 10^{-3}$, $8 \cdot 10^{-3}$ for FIG. 20B) and—the thicker curve—to a measurement. The calculated spectra are modified by the filter absorption, the detector efficiency, and the detector resolution. After adding the constant noise the calculated spectra are normalized in order to compare it with the normalized measured spectrum. Even though there remain some discrepancies between the model and the measured data, the constant noise level within the noise interval can be estimated at $N_c \approx 0.0005$ for the direct beam and $N_c \approx 0.0040$ for the scattered beam. For the direct beam, no target sample was used. Therefore, the noise component which originates from multiple scattering in the sample is not present in this measurement, which results in a considerably lower $N_c$. The discrepancies between the measured flux and the calculated ones originate from an energy dependence of the constant noise component which is ignored because only the noise within the noise interval is of relevance.

In conclusion, the filter can be chosen in three steps:

choosing a nanoparticle material, preferably such that it allows an observation angle close to $\theta=90°$—i.e. having an atomic number of 50 or more.

Making a test measurement (with the target sample, but without XRF material) using this filter with a relatively large thickness so that your measurement is dominated by $N_c$. This allows determining the constant noise flux by fitting the model to the measurement.

Choosing the filter thickness that optimizes the SNR.

For a gold XRF measurement the best material is osmium. Its SNR is only slightly better than the one for iridium but its observation angle of $\theta=93°$ will enhance the SNR even more. The toxicity of osmium might be an argument for the use of iridium.

The following Table 2 shows the expected increase from the existing measurement which was done with $E_{max}$=200 keV with a filter of 150 µm Au+2 mm Cu+2 mm Al.

TABLE 2

| filter material | Os | Ir | Au | Hg |
|---|---|---|---|---|
| atomic number Z | 76 | 77 | 79 | 80 |
| filter-sample shift n | −3 | −2 | 0 | +1 |
| observation angle θ | 93° | 105° | 130° | 140° |
| SNR (U = 200 kV) | 1.65 | 1.49 | 1.00 | 0.94 |
| SNR (U = 640 kV) | 2.72 | 2.48 | 1.77 | 1.67 |

The following issues should also be considered:
as the formulas for the noise and the signal are based on proportionality, the value of the calculated SNR does represent the true SNR with a factor of proportionality. Nevertheless, the values can be used to compare the different conditions (filter material, filter thickness, tube voltage) and to obtain the optimal filter thickness.

The energy resolution of the used X-ray detector system smears the steep theoretical K-edge into the noise interval. Therefore, it is necessary to shift the K-edge to even lower energies in order to position the full XRF peak in a low background environment.

The filter fluorescence lines can be close to the XRF lines of the target. This case can be avoided by using a different selection for the filter material and the observation angle.

Multiple incoherent scattering can shift:
1. Flux from the left side of the unscattered K-edge position to the right side of the single scattered K-edge position by multiple times forward scattering. Example: two times 45° scattering looses less energy than one times 90° scattering, see Table 3 below, corresponding to the case of twofold scattering of Hg K-edge (83.1 keV) X-ray into θ=90°).
2. Flux from the right side of the unscattered K-edge position into the region of the XLF (still the right side of the single scattered K-edge) by a combination of forward and backward scattering.

The filter material can be a compound of two element (one high-Z, one low-Z) in order to make it better for handling; example: use HgS to make a Hg-filter.

The filter can be made of two materials (both high-Z) in order to optimize the detection of two different XRF lines; for example $K_\alpha$ and $K_\beta$.

TABLE 3

| 1st scattering | 2nd scattering | $E_1^{sc}$ [keV] | $E_2^{sc}$ [keV] |
|---|---|---|---|
| +45° | +45° | 79.324 | 75.874 |
| +30° | +60° | 81.330 | 75.335 |
| +60° | +30° | 76.853 | 75.335 |
| +15° | +75° | 82.644 | 73.798 |
| +75° | +15° | 74.163 | 73.798 |
| +90° | +0° | 71.5 | 71.5 |
| +110° | −20° | 68.214 | 67.670 |

REFERENCES

[Hubbell and Seltzer, 1995] J. H. Hubbell and S. Seltzer. Tables of X-Ray Mass Attenuation Coefficients and Mass Energy-Absorption Coefficients 1 keV to 20 MeV for Elements Z=1 to 92 and 48 Additional Substances of Dosimetric Interest. National Institute of Standards and Technology (NIST) publications, May 1995.

[Hubbell and Seltzer, 1999] J. H. Hubbell and S. Seltzer. X-ray mass attenuation coefficients, 1999. http://physics.nist.gov/PhysRefData/XrayMassCoef/cover.html.

Cheng et al. [2012] N. N. Cheng, Z. Starkewolf, R. A. Davidson, A. Sharmah, C. Lee, J. Lien, and T. Guo. Chemical enhancement by nanomaterials under x-ray irradiation. Journal of the American Chemical Society, 134(4):1950-1953, 2012. doi: 10.1021/ja210239k. http://dx.doi.org/10.1021/ja210239k PMID: 22260210.

[Hernandez and Boone 2014] A. M. Hernandez and J. M. Boone. Unfiltered Monte Carlo-based tungsten anode spectral model from 20 to 640 kV. In Medical Imaging 2014: Physics of Medical Imaging, volume 9033 of Proceedings of the International Society for Optical Engineering, page 90334P, March 2014. doi: 10.1117/12.2042295.

The invention claimed is:

1. An apparatus for performing nanoparticle-assisted external beam radiotherapy comprising:
an X-ray spectrometer having an optical axis;
an X-ray filter; and
a mobile holding structure suitable for holding the X-ray filter and the X-ray spectrometer in a first and a second relative position, and for switching from said first to said second relative position while simultaneously allowing the positioning of a patient body part in a target region including a target point;
wherein:
the first and second relative positions of the X-ray filter and the X-ray spectrometer are such that an X-ray beam emitted from an X-ray source crosses the X-ray filter before reaching the target point, a propagation direction of the X-ray beam forming an angle θ different from 0° and 180° with the optical axis of the X-ray spectrometer; and
the second relative position is obtained by inverting the relative positions of the X-ray filter and of the X-ray spectrometer with respect to the patient body part.

2. The apparatus of claim 1, further comprising an X-ray source suitable for emitting the X-ray beam, wherein the X-ray filter is positioned on the propagation axis of the X-ray beam between the X-ray source and the target point and is suitable for attenuating X-rays within a predetermined region of the spectrum of the X-ray beam.

3. The apparatus of claim 2, wherein the angle θ formed by the propagation axis of the X-ray beam and the optical axis of the X-ray spectrometer, measured by considering the optical axis directed towards the spectrometer, is greater than or equal to 90°.

4. The apparatus of claim 2, wherein:
the spectrum of the X-ray beam after crossing the X-ray filter includes a K-edge of at least one metal element having an atomic number Z greater than or equal to 30 ;
the X-ray spectrometer is sensible in a spectral region including at least two distinct fluorescence lines of said metal element or elements; and
the predetermined region of the spectrum of the X-ray beam within which the X-ray filter attenuates X-rays includes two photon energy which, when downshifted by scattering by the angle θ, coincide with said two distinct fluorescence lines.

5. The apparatus of claim 4, wherein said metal element, or each said metal element, has an atomic number Z greater than or equal to 50.

6. The apparatus of claim 5, wherein said or one said metal element is gold and the filter comprises a metal chosen from among osmium and iridium.

7. The apparatus of claim 1, further comprising a processor configured or programmed for:
receiving from the X-ray spectrometer first data representing a first X-ray spectrum acquired with the apparatus set in a first configuration, corresponding to said first relative position of the X-ray filter and of the X-ray spectrometer;
receiving from the X-ray spectrometer second data representing a second X-ray spectrum acquired with the apparatus set in a second configuration, corresponding to said second relative position of the X-ray filter and of the X-ray spectrometer;
processing said first and second data to determine an X-ray dose delivered by the apparatus at a target region surrounding the target point.

8. The apparatus of claim 7, wherein the processor is configured or programmed for:
computing a first intensity ratio between a first and a second fluorescence line contained within the first X-ray spectrum when the apparatus is in its first configuration;
computing a second intensity ratio between the first and the second fluorescence line contained within the second X-ray spectrum when the apparatus is in its second configuration;
computing, from said first and second intensity ratios and from data representing X-ray absorption from bodily tissues, a first and a second X-ray attenuation; and
computing said X-ray dose from said first and second X-ray attenuation, from data representing a spectral flux density of the X-ray beam after crossing the X-ray filter and from data representing X-ray absorption from bodily tissues.

9. The apparatus of claim 8, wherein the processor is further configured or programmed for:
computing a metal nanoparticles mass within the target region from said first and second X-ray attenuation, from data representing a spectral flux density of the X-ray beam after crossing the X-ray filter, from data representing X-ray absorption from bodily tissues and from data representing X-ray fluorescence properties of metal nanoparticles.

10. The apparatus of claim 1, wherein the mobile holding structure is further suitable for holding the X-ray source and for inverting the positions of the X-ray spectrometer and of an ensemble comprising the X-ray source and the X-ray filter relative to the target point.

11. The apparatus of claim 1, wherein the mobile holding structure is further suitable for holding the patient body part and for switching from said first to said second relative position by rotating the patient body part and one among the X-ray spectrometer and an ensemble comprising the X-ray source and the X-ray filter relative to the target point.

12. A method of determining an X-ray dose delivered at a region of a patient body using the apparatus of claim 1, the region of the patient body being positioned at the target point of the apparatus, the method comprising the steps of:
setting the apparatus in a first configuration, corresponding to said first relative position of the X-ray filter and the X-ray spectrometer;
activating the X-ray source, and using the X-ray spectrometer to acquire first data representing a first X-ray spectrum;
setting the apparatus in a second configuration, corresponding to said second relative position of the X-ray filter and the X-ray spectrometer;
activating the X-ray source, and using the X-ray spectrometer to acquire second data representing a second X-ray spectrum; and
processing said first and second data to determine an X-ray dose delivered at a target region surrounding the target point by the apparatus.

13. The method of claim 12 wherein said processing comprises:
computing a first intensity ratio between a first and a second fluorescence line contained within the first X-ray spectrum when the apparatus is in its first configuration;
computing a second intensity ratio between the first and the second fluorescence line contained within the second X-ray spectrum when the apparatus is in its second configuration;
computing, from said first and second intensity ratio and from data representing X-ray absorption from bodily tissues, a first and a second X-ray attenuation; and
computing said X-ray dose from said first and second X-ray attenuations, from data representing a spectral flux density of the X-ray beam after crossing the X-ray filter and from data representing X-ray absorption from bodily tissues.

14. The method of claim 13, further comprising:
computing a metal nanoparticles mass within the target region from said first and second X-ray attenuation, from data representing a spectral flux density of the X-ray beam after crossing the X-ray filter, from data representing X-ray absorption from bodily tissues, and from data representing X-ray fluorescence properties of metal nanoparticles.

* * * * *